United States Patent
Helekar et al.

(10) Patent No.: US 12,186,575 B2
(45) Date of Patent: Jan. 7, 2025

(54) METHOD AND APPARATUS FOR ONCOMAGNETIC TREATMENT

(71) Applicant: THE METHODIST HOSPITAL, Houston, TX (US)

(72) Inventors: Santosh Anand Helekar, Sugar Land, TX (US); David Stuart Baskin, Houston, TX (US); Martyn Alun Sharpe, Houston, TX (US); Kumar Pichumani, Sugar Land, TX (US)

(73) Assignee: THE METHODIST HOSPITAL, Houston, TX (US)

( * ) Notice: Subject to any disclaimer, the term of this patent is extended or adjusted under 35 U.S.C. 154(b) by 785 days.

(21) Appl. No.: 17/293,461

(22) PCT Filed: Nov. 13, 2019

(86) PCT No.: PCT/US2019/061131
§ 371 (c)(1),
(2) Date: May 12, 2021

(87) PCT Pub. No.: WO2020/102312
PCT Pub. Date: May 22, 2020

(65) Prior Publication Data
US 2021/0402199 A1  Dec. 30, 2021

Related U.S. Application Data

(60) Provisional application No. 62/901,128, filed on Sep. 16, 2019, provisional application No. 62/760,779, filed on Nov. 13, 2018.

(51) Int. Cl.
*A61N 2/00* (2006.01)
*A61K 31/19* (2006.01)
(Continued)

(52) U.S. Cl.
CPC .............. *A61N 2/002* (2013.01); *A61K 31/19* (2013.01); *A61K 31/20* (2013.01); *A61N 2/004* (2013.01); *A61N 2/12* (2013.01)

(58) Field of Classification Search
CPC .......... A61N 2/002; A61N 2/004; A61N 2/12; A61K 31/19; A61K 31/20
See application file for complete search history.

(56) References Cited

U.S. PATENT DOCUMENTS

| 4,537,198 A | 8/1985 | Corbett |
|---|---|---|
| 4,967,038 A | 10/1990 | Gevins |

(Continued)

FOREIGN PATENT DOCUMENTS

| CN | 2796743 Y | 7/2006 |
|---|---|---|
| CN | 201216819 Y | 4/2009 |

(Continued)

OTHER PUBLICATIONS

Aleman, A., Use of Repetitive Transcranial Magnetic Stimulation for Treatment in Psychiatry, Clinical Psychopharmacology and Neuroscience, 2013, vol. 11, No. 2, pp. 53-59.

(Continued)

*Primary Examiner* — Samuel G Gilbert
(74) *Attorney, Agent, or Firm* — MARSHALL, GERSTEIN & BORUN LLP

(57) ABSTRACT

To disrupt mitochondrial function in certain cells, controlling hardware causes a magnet to oscillate so as to generate an oscillating magnetic field. The oscillating magnetic field is applied to a volume of tissue including cells with degraded mitochondria to trigger apoptosis in the cells with degraded mitochondria.

17 Claims, 13 Drawing Sheets

(51) Int. Cl.
*A61K 31/20* (2006.01)
*A61N 2/12* (2006.01)

(56) References Cited

U.S. PATENT DOCUMENTS

| | | | |
|---|---|---|---|
| 6,032,677 A | 3/2000 | Blechman et al. | |
| 6,046,046 A | 4/2000 | Hassanein | |
| 6,100,082 A | 8/2000 | Hassanein | |
| 6,123,657 A | 9/2000 | Ishikawa et al. | |
| 6,447,449 B1 | 9/2002 | Fleischman et al. | |
| 6,488,617 B1 | 12/2002 | Katz | |
| 6,673,623 B1 | 1/2004 | Huberman | |
| 6,868,289 B2 | 3/2005 | Palti | |
| 6,953,655 B1 | 10/2005 | Hassanein et al. | |
| 7,013,177 B1 | 3/2006 | Whitehurst | |
| 7,016,725 B2 | 3/2006 | Palti | |
| 7,089,054 B2 | 8/2006 | Palti | |
| 7,136,699 B2 | 11/2006 | Palti | |
| 7,146,210 B2 | 12/2006 | Palti | |
| 7,333,852 B2 | 2/2008 | Palti | |
| 7,467,011 B2 | 12/2008 | Palti | |
| 7,519,420 B2 | 4/2009 | Palti | |
| 7,565,205 B2 | 7/2009 | Palti | |
| 7,565,206 B2 | 7/2009 | Palti | |
| 7,572,622 B2 | 8/2009 | Hassanein et al. | |
| 7,599,745 B2 | 10/2009 | Palti | |
| 7,599,746 B2 | 10/2009 | Palti | |
| 7,651,835 B2 | 1/2010 | Hassanein et al. | |
| 7,706,890 B2 | 4/2010 | Palti | |
| 7,715,921 B2 | 5/2010 | Palti | |
| 7,805,201 B2 | 9/2010 | Palti | |
| 7,890,183 B2 | 2/2011 | Palti et al. | |
| 7,912,540 B2 | 3/2011 | Palti | |
| 7,917,227 B2 | 3/2011 | Palti | |
| 8,019,414 B2 | 9/2011 | Palti | |
| 8,027,738 B2 | 9/2011 | Palti | |
| 8,170,684 B2 | 5/2012 | Palti | |
| 8,175,698 B2 | 5/2012 | Palti et al. | |
| 8,229,555 B2 | 7/2012 | Palti | |
| RE43,618 E | 8/2012 | Palti | |
| 8,244,345 B2 | 8/2012 | Palti | |
| 8,304,181 B2 | 11/2012 | Hassanein et al. | |
| 8,406,870 B2 | 3/2013 | Palti | |
| 8,409,846 B2 | 4/2013 | Hassanein et al. | |
| 8,420,380 B2 | 4/2013 | Fishman et al. | |
| 8,447,395 B2 | 5/2013 | Palti et al. | |
| 8,447,396 B2 | 5/2013 | Palti et al. | |
| 8,465,533 B2 | 6/2013 | Palti | |
| 8,465,970 B2 | 6/2013 | Hassanein et al. | |
| 8,535,934 B2 | 9/2013 | Hassanein et al. | |
| 8,560,073 B2 | 10/2013 | Osorio | |
| 8,585,380 B2 | 11/2013 | Hassanein et al. | |
| 8,706,261 B2 | 4/2014 | Palti | |
| 8,715,203 B2 | 5/2014 | Palti | |
| 8,718,756 B2 | 5/2014 | Palti | |
| 8,764,675 B2 | 7/2014 | Palti | |
| 8,822,203 B2 | 9/2014 | Hassanein et al. | |
| 8,888,672 B2 | 11/2014 | Phillips et al. | |
| 9,023,090 B2 | 5/2015 | Palti | |
| 9,023,091 B2 | 5/2015 | Palti | |
| 9,039,674 B2 | 5/2015 | Palti et al. | |
| 9,055,740 B2 | 6/2015 | Hassanein et al. | |
| 9,056,203 B2 | 6/2015 | Palti et al. | |
| 9,078,428 B2 | 7/2015 | Hassanein et al. | |
| 9,215,867 B2 | 12/2015 | Hassanein et al. | |
| 9,247,728 B2 | 2/2016 | Fishman et al. | |
| 9,272,159 B2 | 3/2016 | Phillips et al. | |
| 9,301,519 B2 | 4/2016 | Hassanein et al. | |
| 9,440,068 B2 | 9/2016 | Palti et al. | |
| 9,456,784 B2 | 10/2016 | Helekar et al. | |
| 9,457,179 B2 | 10/2016 | Hassanein et al. | |
| 9,462,802 B2 | 10/2016 | Fishman et al. | |
| 9,516,875 B2 | 12/2016 | Fishman et al. | |
| 9,655,669 B2 | 5/2017 | Palti et al. | |
| 9,750,934 B2 | 9/2017 | Palti et al. | |
| 9,756,849 B2 | 9/2017 | Hassanein et al. | |
| 9,756,850 B2 | 9/2017 | Hassanein et al. | |
| 9,756,851 B2 | 9/2017 | Hassanein et al. | |
| 9,814,230 B2 | 11/2017 | Fishman et al. | |
| 9,894,894 B2 | 2/2018 | Hassanein et al. | |
| 9,910,453 B2 | 3/2018 | Wasserman et al. | |
| 10,039,276 B2 | 8/2018 | Hassanein et al. | |
| 10,076,112 B2 | 9/2018 | Hassanein et al. | |
| 10,188,851 B2 | 1/2019 | Wenger et al. | |
| 10,194,655 B2 | 2/2019 | Ritchie et al. | |
| 10,314,303 B2 | 6/2019 | Hassanein et al. | |
| 10,321,676 B2 | 6/2019 | Hassanein et al. | |
| 10,327,443 B2 | 6/2019 | Hassanein et al. | |
| 10,398,907 B2 | 9/2019 | Helekar et al. | |
| 10,500,408 B2 | 12/2019 | Helekar et al. | |
| 10,874,870 B2 | 12/2020 | Helekar et al. | |
| 11,571,585 B2 * | 2/2023 | Helekar | A61N 2/06 |
| 2002/0151760 A1 | 10/2002 | Paturu | |
| 2004/0193001 A1 | 9/2004 | Miller | |
| 2005/0079132 A1 * | 4/2005 | Wang | A61N 2/06 424/1.11 |
| 2005/0228209 A1 | 10/2005 | Schneider et al. | |
| 2006/0015153 A1 | 1/2006 | Gliner et al. | |
| 2006/0094924 A1 | 5/2006 | Riehl | |
| 2006/0122454 A1 | 6/2006 | Riehl et al. | |
| 2006/0265022 A1 | 11/2006 | John | |
| 2006/0282122 A1 | 12/2006 | Palti | |
| 2007/0093706 A1 | 4/2007 | Gevins | |
| 2007/0260107 A1 | 11/2007 | Mishelevich et al. | |
| 2008/0014285 A1 | 1/2008 | Di Mauro et al. | |
| 2008/0312706 A1 | 12/2008 | Zangen et al. | |
| 2009/0082690 A1 | 3/2009 | Phillips et al. | |
| 2010/0185042 A1 | 7/2010 | Schneider et al. | |
| 2010/0210894 A1 | 8/2010 | Pascual-Leone et al. | |
| 2010/0249488 A1 | 9/2010 | Kardos et al. | |
| 2011/0015469 A1 | 1/2011 | Walter et al. | |
| 2011/0034822 A1 | 2/2011 | Phillips et al. | |
| 2011/0105826 A1 | 5/2011 | Mishelevich et al. | |
| 2011/0112427 A1 | 5/2011 | Phillips et al. | |
| 2011/0118536 A1 | 5/2011 | Phillips et al. | |
| 2011/0118636 A1 | 5/2011 | Kitamura et al. | |
| 2011/0137104 A1 | 6/2011 | Phillips et al. | |
| 2011/0184223 A1 | 7/2011 | Peterchev et al. | |
| 2011/0270345 A1 | 11/2011 | Johnston et al. | |
| 2012/0053449 A1 | 3/2012 | Moses et al. | |
| 2012/0057752 A1 | 3/2012 | Li et al. | |
| 2012/0157752 A1 | 6/2012 | Nishikawa | |
| 2013/0090545 A1 | 4/2013 | Flynn | |
| 2013/0137918 A1 | 5/2013 | Phillips et al. | |
| 2014/0163305 A1 | 6/2014 | Watterson | |
| 2014/0179980 A1 | 6/2014 | Phillips et al. | |
| 2014/0200388 A1 | 7/2014 | Schneider et al. | |
| 2014/0276182 A1 | 9/2014 | Helekar et al. | |
| 2014/0276812 A1 | 9/2014 | Batchelor et al. | |
| 2016/0008620 A1 | 1/2016 | Stubbeman | |
| 2016/0193476 A1 | 7/2016 | Helekar et al. | |
| 2017/0136255 A1 | 5/2017 | Helekar et al. | |
| 2017/0215939 A1 | 8/2017 | Palti et al. | |
| 2017/0224990 A1 | 8/2017 | Goldwasser et al. | |
| 2017/0281934 A1 | 10/2017 | Giladi et al. | |
| 2018/0001075 A1 | 1/2018 | Kirson et al. | |
| 2018/0001078 A1 | 1/2018 | Kirson et al. | |
| 2018/0008708 A1 | 1/2018 | Giladi et al. | |
| 2018/0050200 A1 | 2/2018 | Wasserman et al. | |
| 2018/0160933 A1 | 6/2018 | Urman et al. | |
| 2018/0202991 A1 | 7/2018 | Giladi et al. | |
| 2018/0214710 A1 | 8/2018 | Charles et al. | |
| 2018/0229049 A1 | 8/2018 | Phillips et al. | |
| 2018/0350451 A1 | 12/2018 | Ohnemus et al. | |
| 2019/0117956 A1 | 4/2019 | Wenger et al. | |
| 2019/0381333 A1 | 12/2019 | Helekar et al. | |
| 2020/0139147 A1 | 5/2020 | Helekar et al. | |

FOREIGN PATENT DOCUMENTS

| | | |
|---|---|---|
| CN | 105188844 A | 12/2015 |
| DE | 10 2011 050507 A1 | 11/2012 |
| EP | 2 968 968 A2 | 1/2016 |
| EP | 3 033 007 A4 | 5/2017 |

(56) References Cited

FOREIGN PATENT DOCUMENTS

| WO | WO-2005/051306 A2 | 6/2005 |
|---|---|---|
| WO | WO-2009/033150 A1 | 3/2009 |
| WO | WO-2009/036040 A1 | 3/2009 |
| WO | WO-2010/025114 A1 | 3/2010 |
| WO | WO-2011/017466 A1 | 2/2011 |
| WO | WO-2012/126044 A1 | 9/2012 |
| WO | WO-2014/152827 A2 | 9/2014 |
| WO | WO-2015/023980 A2 | 2/2015 |
| WO | WO-2016/059556 A1 | 4/2016 |

OTHER PUBLICATIONS

Amassian, V. E et al., Transcranial Magnetic Stimulation in Study of the Visual Pathway, Journal of Clinical Neurophysiology, 1998, 15(4): 288-304.
Antal, A. et al., Electrical Stimulation and Visual Network Plasticity, Restorative Neurology and Neuroscience, 2011, vol. 29, pp. 365-374.
Azanon, E. et al., Somatosensory processing and body representation, Cortex 45, 2009, 1078-1084.
Beauchamp, M. S. et al., fMRI-Guided Transcranial Magnetic Stimulation Reveals That the Superior Temporal Sulcus is a Cortical Locus of the McGurk Effect, The Journal of Neuroscience, 2010, 30(7): 2414-7.
Beckers, G. et al., Cerebral visual motion blindness: transitory akinetopsia induced by transcranial magnetic stimulation of human area V5, Proceedings: Biological Sciences, 1992, 249(1325): 173-8.
Bikson, M. et al., Effects of Uniform Extracellular DC Electric Fields on Excitabiity in Rai Hippocampal Slices in Vitro, Journal of Physiology, 2004, vol. 557, pp. 175-190.
Buch, E. R. et al., Noninvasive Associative Plasticity Induction in a Corticocortical Pathway of the Human Brain, The Journal of Neuroscience, 2011, 31(48): 17669-79.
Cardenas-Morales, L. et al., Mechanisms and Applications of Theta-Burst rTMS on the Human Motor Cortex, Brain Topogr, 2010, vol. 22, pp. 294-306.
Chen, R. et al., The Clinical Diagnostic Utility of Transcranial Magnetic Stimulation: Repost of an IFCN Committee, Clinical Neurophysiology, 2008, vol. 119, pp. 504-532.
Dayan, Eran et al., Noninvasive brain stimulation: from physiology to network dynamics and back, Nature Neuroscience, Jul. 2013, vol. 16, No. 7.
De Pasquale et al., A Cortical Core for Dynamic Integration of Functional Networks in the Resting Human Brain, Neuron, 2012, 74(4): 753-64.
De Ridder, D. et al., Primary and Secondary Auditory Cortex Stimulation for Intractable Tinnitus, ORL, 2006, 68(1): 48-54.
Deans, J.K. et al,, Sensitivity of Coherent Oscillations in Rat Hippocampus to AC Electric Fields, Journal of Physiology, 2007, vol. 583, pp. 555-565.
Deco, G. et al., Ongoing Cortical Activity at Rest: Criticality, Multistability, and Ghost Attractors, The Journal of Neuroscience, 2012, 32(10): 3366-75.
Dell'Osso, B. et al., Meta-Review of Metanalytic Studies with Repetitive Transcranial Magnetic Stimulation (rTMS) for the Treatment of Major Depression, Clinical Practice & Epidemiology in Mental Health, 2011, 7, 167-77.
Delvendahl, I. et al., Plasticity of motor threshold and motor-evoked potential amplitude—A model of intrinsic and synaptic plasticity in human motor cortex?, Brain Stimulation 5, 2012, 586-593.
Devlin, J. T. et al., Stimulating language: insights from TMS, Brain, 2007, 130, 610-22.
Di Lazzaro, V. et al., Modulation of Motor Cortex Neuronal Networks by rTMS: Comparison of Local and Remote Effects of Six Different Protocols of Stimulation, Journal of Neurophysiology, 2011, vol. 105, pp. 2150-2156.
Esser, S.K. et al., Modeling the Effects of Transcranial Magnetic Stimulation on Cortical Circuits, Journal of Physiology, 2005, vol. 94, pp. 622-639.

Examination Report for BR Application No. 112015022834-8, dated Jul. 5, 2020.
Examination Report for BR Application No. 112016003147-4, dated Aug. 11, 2020.
Extended European Search Report for Application No. 14771163.4, dated Jan. 3, 2017.
Extended European Search Report for Application No. 14836452.4, dated May 2, 2017.
Farina, D. et al., Detecting the Unique representation of the Motor-Unit Action Potentials in the Surface Electromyogram, Journal of Neurophysiology, 2008, vol. 100, pp. 1223-1233.
First Examination Report for IN Application No. 201617008498, dated May 19, 2020.
First Examination Report for IN Application No. 9216/DELNP/2015, dated Jun. 5, 2020.
First Office Action for Chinese Application No. 201480027788.3, dated Oct. 10, 2016.
First Office Action for Chinese Application No. 201480057016.4, dated May 28, 2018.
Fitzgerald, P. B. et al., GABA and cortical inhibition in motor and non-motor regions using combined TMS-EEG: A time analysis, Clinical Neurophysiology 120, 2009, 1706-1710.
Fox, M. D. et al., The human brain is intrinsically organized into dynamic, anticorrelated functional networks, Proceedings of the National Academy of Sciences of the USA, 2005, vol. 102, No. 27, 9673-8.
Fregni, F. et al., Technology Insight: NonInvasice Brain Stimulation in Neurology: Perspectives on the Therapeutic Potential of rTMS and tDCS, Nature Clinical Practice Neurology, 2007, vol. 3, pp. 1-11.
Frohlich, F. et al., Endogenous Electric Fields May Guide Neocortlcai Network Activity, Neuron, Jul. 15, 2010, vol. 67, pp. 129-143.
Frye, R.E. et al., Transcranial Magnetic Stimulation in Child Neurology: Current and Future Directions, Journal of Child Neurology, Jan. 2008, vol. 23, No. 1, pp. 79-96.
George, M.S. et al., the Expanding Evidence Base for rTMS Treatment of Depression, Current Opinion on Psychiatry, Jan. 2013, vol. 26, No. 1, pp. 13-18.
Gonzalez-Rosa, J.J. et al.., Static Magnetic Field Stimulation over the Visual Cortex increases Alpha Oscillations and Slows Visual Search in Humans, The Journal of Neuroscience, Jun. 17, 2015, vol. 35, No. 24, pp. 9182-9193.
Guse, B. et al., Cognitive effects of high-frequency repetitive transcranial magnetic stimulation: a systematic review, Journal of Neural Transmission, 2010, 117: 105-22.
Helekar Santosh A., In Defense of Experience—Coding Nonarbitrary Temporal Neural Activity Patterns, Consciousness and Cognition, Dec. 1999, pp. 455-461, vol. 8, issue 4.
Helekar, S.A. et al., Electromyographic motor-evoked potentials elicited by transcranial magnetic stimulation with rapidly moving permanent magnets mounted on a multisite stimulator cap, Presentation Abstract, Nov. 13, 2013.
Helekar, Santosh A., On the Possibility of Universal Neural Coding of Subjective Experience, Consciousness and Cognition, Dec. 1999, pp. 423-446, vol. 8, Issue 4.
Helekar, Santosh et al., Transcranial Brain Simulation With Rapidly Spinning High-Field Permanent Magnets, IEEE Access, vol. 4, May 19, 2016, pp. 2520-2527.
Helfrich, R.F. et al., Entrainment of Brain Oscillations by Transcranial Alternating Current Stimulation, Current Biology, Feb. 3, 2014, vol. 24, pp. 333-339.
Huerta, P. T. et al., Transcranial magnetic stimulation, synaptic plasticity and network oscillations, Journal of NeuroEngineering and Rehabilitation, 2009, 6:7.
Llic, T. V. et al., Exploring Motor Cortical Plasticity Using Transcranial Magnetic Stimulation in Humans, Annals of the New York Academy of Sciences, 2005, vol. 1048(1): 175-184.
International Preliminary Report on Patentability for Application No. PCT/US2014/027900, dated Sep. 15, 2015.
International Preliminary Report on Patentability for Application No. PCT/US2014/051340, dated Feb. 16, 2016.
International Preliminary Report on Patentability for Application No. PCT/US2017/031413, dated Nov. 15, 2018.

(56) References Cited

OTHER PUBLICATIONS

International Search Report and Written Opinion for Application No. PCT/US2014/027900, dated Sep. 4, 2014.
International Search Report and Written Opinion for Application No. PCT/US2014/051340, dated Apr. 15, 2015.
International Search Report and Written Opinion for Application No. PCT/US2017/031413, mailing date Aug. 14, 2017.
International Search Report and Written Opinion for Application No. PCT/US2019/061131, dated Apr. 28, 2020.
Jin, Y. et al., A Pilot Study of the Use of EEG-Based Synchornlzed Transcranial Magnetic Stimulation (sTMS) for Treatment of Major Depression, BMC Psychiatry, 2014, Voi. 14, No. 13, pp. 1-6.
Kamitani, Y. et al., Manifestation of scotomas created by transcranial magnetic stimulation of human visual cortex, Nature Neuroscience, 1999, 2(8): 767-71.
Kamke, M. R. et al., Parietal disruption alters audiovisual binding in the sound-induced flash illusion, Neurolmage 62, 2012, 1334-1341.
Kammer, T., Masking visual stimuli by transcranial magnetic stimulation, Psychological Research, 2007, 71: 659-66.
Leuchter, A. F. et al., Synchronized Transcranial Magnetic Stimulation (sTMS) Efficacy and Safety of Low-field Synchronized Transcranial Magnetic Stimulation (sTMS) for Treatment of Major Depression, Brain Stimulation, 2015, 1-8.
Levasseur-Moreau, J. et al., Translational application of neuromodulation of decision-making, Brain Stimulation 5, 2012, 77-83.
Lipton, R. B. et al., Transcranial Magnetic Simulation in the Treatment of Migraine, Neurotherapeutics: The Journal of the American Society for Experimental Neuro Therapeutics, 2010, vol. 7, 204-12.
Muller, P. A. et al., Safety and tolerability of repetitive transcranial magnetic stimulation in patients with pathologic positive sensory phenomena: a review of literature, Brain Stimulation, 2012, 5(3): 320-329.
Muller-Dahlhaus, F. et al., Plasticity resembling spike-timing dependent synaptic plasticity: the evidence in human cortex, Frontiers in Synaptic Neuroscience, 2010, vol. 2, Article 34, 1-11.
Nakatani-Enomoto, S. et al., Bidirectional modulation of sensory cortical excitability by quadripulse transcranial magnetic stimulation (QPS) in humans, Clinical Neurophysiology 123, 2012, 1415-1421.
Office Action for Canadian Application No. 2,942,653, dated August 7. 2020.
Office Action for Canadian Application No. 2,942,653, dated Jul. 19, 2019.
Office Action for Canadian Application No. 2,942,653, dated Jun. 18, 2021.
Office Action, European Patent Application No. 14771163.4, mailing date Mar. 20, 2019.
Olivierg, A. et al., Transcranial Static Magnetic Field Stimulation of the Human Motor Cortex, Journal of Physiology, 2011, vol. 589, No. 20, pp. 4949-4958.
Pitcher, D. et al., Transcranial Magnetic Stimulation Disrupts the Perception and Embodiment of Facial Expressions, The Journal of Neuroscience, 2008, 28(36): 8929-33.
Rivadulla, C. et al., Magnetic Field Strength and Reproducibility of Neodymium Magnets Usefui for Transcranial Static Magnetic Field Stimulation of the Human Cortex, Neuromodulation: Technology at the Neural interface, 2014, vol. 17, No. 5, pp. 438-442.
Rossi S. et al., Safety, ethical considerations, and application guidelines for the use of transcranial magnetic stimulation in clinical practice and research, Clinical Neurophysiology, 2009, 2008-2039.
Sanchez, Alvaro et al., Antimagnets: Controlling Magnetic Fields With Superconductor—Metamaterial Hybrids, New Journal of Physics, 2011, vol. 13.
Sandrini, M. et al., The use of transcranial magnetic stimulation in cognitive neuroscience: A new synthesis of methodological issues, Neuroscience and Biobehavioral Reviews 35, 2011, 516-536.
Second Office Action for Chinese Application No. 201480027788.3, dated Aug. 14, 2017.
Second Office Action for Chinese Application No. 201480057016.4, dated Apr. 3, 2019.
Thielscher, A, et al., Linking Physics with Physiology in TMS: A Sphere Field Model to Determine the Cortical Stimulation Site in TMS, Neuroimage, 2002, vol. 17, pp. 1117-1130.
Third Office Action for Chinese Application No. 201480027788.3, dated Mar. 6, 2018.
Third Office Action for Chinese Application No. 201480057016.4, dated Sep. 12, 2019.
Wassermann, E. M. et al., Transcranial Magnetic Brain Stimulation: Therapeutic Promises and Scientific Gaps, Pharmacology and Therapeutics, 2012, 133(1): 98-107.
Wassermann, E. M., Risk and safety of repetitive transcranial magnetic stimulation: report and suggested guidelines from the International Workshop on the Safety of Repetitive Transcranial Magnetic Stimulation, Jun. 5-7, 1996, Electroencephalographyand Clinical Neurophysiology, 1998, 108, 1-16.
Zaehle, T. et al., Transcranial Alternating Current Stimulation Enhances Individual Alpha Activity in Human EEG, PloS one, Nov. 2010, vol. 5, No. 11, pp. 1-7.

\* cited by examiner

METHOD AND APPARATUS FOR ONCOMAGNETIC TREATMENT

CROSS-REFERENCE TO RELATED APPLICATION

This present application is the US national phase of International Patent Application No. PCT/US2019/061131, filed Nov. 13, 2019, which claims priority to U.S. Provisional Patent Application No. 62/760,779, filed Nov. 13, 2018 and U.S. Provisional Patent Application No. 62/901,128, filed Sep. 16, 2019, the entire disclosures of which are hereby expressly incorporated by reference herein.

FIELD OF THE DISCLOSURE

This disclosure generally relates to cancer treatment methods and apparatus and, more particularly, to non-invasive cancer treatments utilizing oscillating magnetic fields.

BACKGROUND

Cancer is one of the biggest health problems facing modern society, and improvements in aggressive treatments for some forms of cancer, including glioblastoma—(GBM) remain dismal. Common forms of cancer treatment include chemotherapy and radiotherapy which can be devastating to the patient's body, causing severe physical and mental trauma. The heavy toll on patients can result in a patient deciding not to complete the suggested chemotherapy or radiation treatment cycles. Thus, there is a need for a cancer treatment approach with better life-expectancy outcome and less toxicity.

Recently, applying alternating electric fields (AEFs) to the scalp, a treatment called Tumor Treating Field (TTF) therapy or Optune® therapy, has shown therapeutic benefit in patients with GBM. TTF therapy has been approved by the U.S. Food and Drug Administration as monotherapy for GBM and in combination with other therapies for newly diagnosed GBM. TTF therapy is commonly administered to patients by attaching electrodes to a patient's head, which requires shaving the patient's head at electrode sites. Moreover, electrodes often cause lesions on the skin, rashes, other dermatological adverse effects, and in some cases even cause burns due to applied electrical currents.

SUMMARY

Generally speaking, the system of this disclosure causes apoptosis, or a molecular cell death, in cancer cells by rapidly oscillating one or more magnets to generate an oscillating magnetic field (OMF) to disrupt electron flow; for example in the mitochondrial electron transport chain (ETC), thereby disrupting mitochondrial function. The system can apply OMFs without directly contacting the subject's scalp when used treat to a brain tumor, or the subject's skin when used with other parts of the body.

The system can include one or more stimulators, each including a permanent magnet and an electric motor configured to communicate oscillating motion (e.g., rotation, translational oscillation) to the permanent magnet. Advantageously, these techniques do not require passing a large current through coils or solenoids, for example. In some implementations, the stimulators are miniaturized and are referred to as "microstimulators." When the system includes multiple stimulators, the controlling hardware can cause the stimulators to operate at different times, at different frequencies, at different pulse rates, etc. to define a particular stimulation pattern, which can be subject-specific.

One example embodiment of these techniques is a method for disrupting mitochondrial function in cells. The method includes causing, by controlling hardware, a magnet to oscillate so as to generate an oscillating magnetic field, and applying the oscillating magnetic field to a volume of tissue including cells with mitochondrial impairment to trigger apoptosis in the cells with mitochondrial impairment.

Another example embodiment of these techniques is a system for disrupting mitochondrial function in cells. The system includes at least one stimulator/oscillator including a magnet and a controlling hardware configured to cause the magnet to oscillate so as to generate an oscillating magnetic field that, when applied to a volume of tissue including cells with mitochondrial impairment, triggers apoptosis in the cells with the mitochondrial impairment.

Yet another example embodiment of these techniques is a method for disrupting mitochondrial function in cancer cells. The method includes generating, in a tissue including cancer cells, the disruption of electrons to cause apoptosis in the cancer cells through (i) a decrease in mitochondrial glucose oxidation in glucose oxidation in a tricarboxylic acid (TCA) cycle, (ii) an increase in a metabolic flux of glycolysis, (iii) an increase in superoxide, peroxide and other reactive oxygen species generation, (iv) the opening of the mitochondrial membrane permeability transition pore, (v) an increase in fission of mitochondrial networks in the cancer cells, and/or (vi) activation of caspase-3-mediated apoptotic pathway or an alternate apoptotic mechanism in the cancer cells.

DETAILED DESCRIPTION

Figure 1:
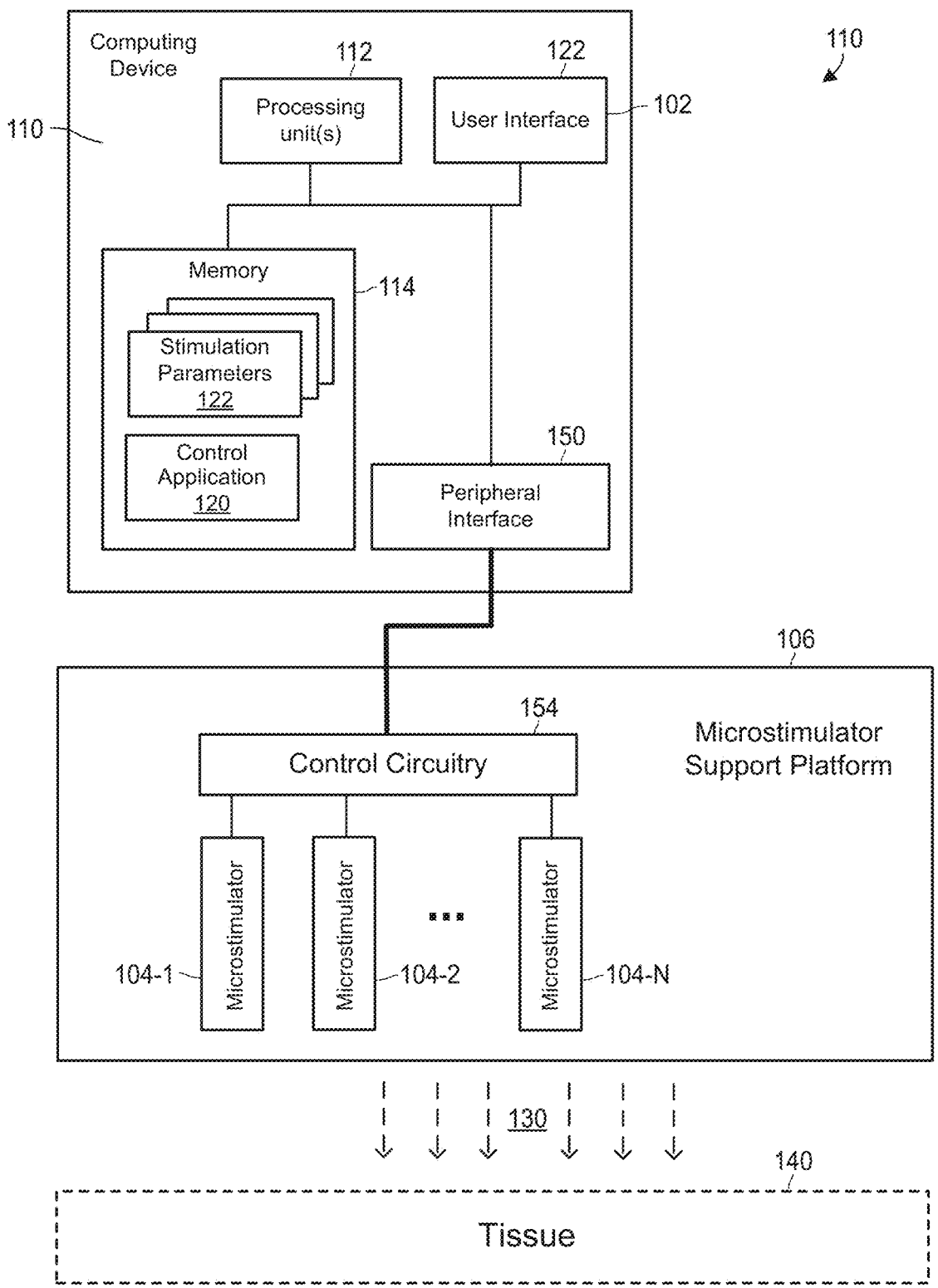
FIG. 1 is a block diagram of a system for disrupting mitochondrial function in certain cells by applying a rapidly changing magnetic field, according to one example implementation.

Effect of Oscillating Electromagnetic Fields on Tumors

A system of this disclosure applies oscillating magnetic fields, and more particularly, rapidly changing magnetic fields, to tissue so as to target cancer cells. Generally speaking, cancer cells have altered bioenergetics, mitochondrial function, and a reduced number of mitochondria due to uncontrolled cell division. One such alteration seen in these cells due to mutations in the electron transport chain which may play a role in carcinogenicity (i.e., inducing of tumors). The system of disclosure uses the anti-cancer effects of oscillating magnetic fields on tumors. Evidence suggests that these anti-cancer effects are due to changes in the fluxes through bioenergetic and redox mechanisms in cancer cells. The methods and apparatus disclosed employ oscillating magnetic fields generated by rapid rotation or translation of strong permanent magnets with high field strengths. The application of the oscillating magnetic field causes a substantial decrease in the flux through the reductive carboxylation pathway in patient-derived GBM cells, which might be related to the anti-cancer effect.

Glutamine is an essential amino acid with many functions including being a major bioenergetic nutrient for cancer cells. Glutamine provides energy and carbon precursors for macromolecular synthesis that is required for biomass production, and specifically glutamine acts as an energy source for rapidly dividing cells. Aside from glucose, glutamine is the most rapidly consumed nutrient by many types of cultured cancer cells. Glutamine is converted to glutamate upon entering the cells by glutaminase (GLS), which enters the tricarboxylic acid (TCA) cycle through the conversion into α-ketoglutarate (α-KG) by glutamate to generate oxaloacetate (OAA), citrate and other TCA cycle intermediates. Citrate is an important 6 carbon TCA cycle intermediate that is necessary to maintain mitochondrial oxidative metabolism and cytosolic biomolecular synthesis. Mitochondrial citrate is generated through multiple nutrient sources. Glucose-derived pyruvate produces acetyl-CoA via pyruvate dehydrogenase (PDH) that condenses with OAA to generate citrate. In many cancer cells, pyruvate carboxylase acts as a major anaplerotic pathway that also generates citrate from pyruvate through the production of OAA in the TCA cycle. Cancer cells with altered mitochondrial function (due to either mutations in electron transport chain (ETC) or tricarboxylic acid cycle enzymes) are capable of generating citrate through reductive carboxylation of glutamine-derived α-ketoglutarate. ATP-citrate lyase (ACL) cleaves exported citrate in the cytosol to produce acetyl-CoA which is further used as precursor for lipid de novo synthesis.

The system of this disclosure uses electromagnetic fields (EMF) to modulate cellular metabolism. Long exposures to repeated EMF pulses, radiating radiofrequency waves, or non-radiating local field oscillations have varying degrees of efficacy against cancer cells in culture. Cancer cells are oxidatively stressed, compared to normal cells of the same tissue, and have high levels of reactive oxygen species (ROS) which, if accentuated further, leads to cancer cell apoptosis. The application of EMF pulses on cells causes an increase in the intracellular levels of ROS leading to cell apoptosis. Disclosed herein are methods and systems for generating an oscillating magnetic field (OMF) for in vitro and in vivo treatment of tumors and cancerous tissue by inducing the generation of ROS and causing cancer cell apoptosis.

As described herein, "magnetic stimulators" or "microstimulators" generate OMFs through the rotation of permanent magnets at high speeds. The microstimulators are modified to produce patterns of magnetic field oscillations that cause selective apoptosis of cultured GBM cells, without causing apoptosis in normal astrocytes. The lack of lethality in normal cells is due to an abundance of mitochondria, absent or reduced oxidative stress, and much lower demand for ATP compared to rapidly dividing malignant cells. In fact, repetitive transcranial magnetic stimulation has shown decreased apoptosis in non-cancerous cells. By applying OMFs at certain ranges of frequencies applied in defined pulsed patterns, the system causes the disruption of electron flow in the mitochondrial electron transfer chain (ETC), in turn causing the generation of ROS. The ROS cause the opening of the mitochondrial permeability transition pore (MPTP), resulting in mitochondrial membrane depolarization and extrusion of cytochrome C, and triggering caspase-dependent apoptosis or apoptosis by an alternate mechanism in the cancer cell. The microstimulators may also be referred to herein as oncoscillators due to the tumor-tissue selective nature of the treatment methods and systems described herein. In various embodiments, the systems can include microstimulator probes, wearable apparatus with multiple oncoscillators, and fixtures for surrounding a patient or body of tissue for treatment.

The OMF therapy methods and systems described do not have the limitations of chemotherapeutic agents such as the need for adequate blood supply to all parts of the malignant tumor, the ability to penetrate the blood brain barrier in case of brain cancers, a high enough bioavailability, a favorably tuned pharmacokinetic profile, a sufficiently large therapeutic index, etc. In addition, a variety of OMF treatment delivery mechanisms are available with great flexibility and versatility to have a substantial impact on all types of primary and metastatic solid neoplasms, and possibly systemic malignancies as well. Additionally, it is possible to administer OMF treatment sessions as only one to three hours of application a day, whereas TTF therapy requires 18 to 20 hours of treatment each day. The proposed methods and systems for OMF therapy cost much less than TTF therapy. The specific OMF frequencies and amplitudes selectively kill cancer cells in any stage of the cell cycle and do not depend on cell division, depend on being in a mitotic state, or depend on any other state. In fact, the methods and systems disclosed can selectively kill cancer cells in the G0 phase of the cell cycle. The method and systems for oncomagnetic therapy described herein can be drug-free, ionizing radiation-free, and non-invasive, or oncomagnetic therapy may be performed in conjunction with other forms of therapy such as with chemotherapy, other forms of radiative therapy, with drugs and prescriptions, etc.

According to at least some of the techniques of this disclosure, a system generates oscillating magnetic fields to induce alteration of electron flow in a tissue. However, it is believed that at least some of these techniques also can be used with AEF techniques to eliminate the need to directly apply electrodes to the patient's skin, for example. More particularly, it may be possible to use oscillating magnets to generate AEFs with properties similar to those used in TTF therapy.

An Example System for Disrupting Mitochondrial Function in Cells

FIG. 1 illustrates an example implementation system 100 for disrupting mitochondrial function in certain cells by applying a rapidly changing magnetic field. The system 100 includes a computing device 102 that controls magnetic stimulators 104-1, 104-2, . . . 104-N mounted on a stimulator support platform 106, which can be a probe, helmet, a brace, a belt, mechanical frame, room, bed, cubicle, etc. Because the stimulators 104 can be miniaturized to be, for example, 500 millimeters, 1 cm, 2 cm, etc. along the longest dimension, the magnetic stimulators 104 are referred to below as microstimulators 104. Further, due to the particular application of the magnetic fields discussed herein, the magnetic stimulators 104 can be referred to as "oncoscillators." The computing device 102 includes controlling hardware 110 that can include one or more processing units 112 coupled to a non-transitory computer-readable memory 114 storing a control application 120 and stimulation parameters 122.

In operation, the controlling hardware 110 causes the microstimulators 104 to generate an oscillating magnetic field 130 and, using the stimulator support platform 106, apply the oscillating magnetic field 130 to a tissue 140. The microstimulators 104 generate the oscillating magnetic field 130 in a manner that causes disruption of mitochondrial function in cells of the tissue 140. As discussed in more detail below, the oscillating magnetic field 130 disrupts electron flow in the cells, such that apoptosis is triggered in the cancer cells, but no apoptosis is triggered in the healthy cells of the tissue 140.

In addition to being capable of altering electron flow in cell tissue without directly contacting the subject's scalp or skin on other parts of the body, the system 100 provides an additional advantage of being configurable for a variety of different solid cancers. As discussed below, various stimulation parameters and stimulation parameters can generate different configurations of OMF, which can be tailored for a specific cell type and/or specific subject to implement a personalized treatment protocol. Further, the system has the advantage of an imperceptible sham treatment capability to serve as a placebo control in double-blind trials. In particular, high-field strength magnets in the microstimulators discussed below can be replaced with demagnetized magnets. Because a human subject cannot sense the magnetic field, research subject and investigators cannot distinguish between an operational instance of the system 100 and a sham stimulation system by inspection or during a treatment session.

The computing device 102 can be a general-purposed computing device such as a desktop computer, a laptop computer, a table computer, a smartphone, a wearable device such as a smartwatch, etc. The one or more processing units 112 in these implementations can be central processing units (CPUs), and the memory 114 can include persistent components (e.g., a flash drive, a disk) as well as non-persistent components (e.g., Random Access Memory (RAM)). In other implementations, the computing device 102 is a special-purpose medical device configured specifically to control the one or more microstimulators 104. The processing units 112 in this case can include a field programmable gate array (FPGA), an application-specific integrated circuit (ASIC), or any other type of special-purpose hardware. Further, the controlling hardware 110 in some implementations is embedded in the stimulator support platform 106.

The control application 120 can and one or more sets of stimulation parameters 122 which can specify, for a certain stimulation session, at least some of: the duration of the session, pulse width (length) of stimulus pulses, the duration of stimulus pulse intervals, and the frequency of oscillation of the magnets. The stimulation parameters 122 in some cases can define separate sets of values for different microstimulators 104-1, 104-2, . . . 104-N, to define a particular stimulation pattern. More particularly, the stimulation pattern can specify a certain time of activation and operational parameters (frequency, pulse parameters) for the microstimulator 104-1, specify a different time of activation and different operational parameters for the microstimulator 104-2, etc. These parameters in some cases can depend on the relative positioning of the microstimulators 104, so that for example a microstimulator 104-$i$ and a microstimulator 104-$j$ positioned at a certain distance and oriented at a certain angle relative to each other generate stimulation pulses with a certain phase offset, so as to generate an oscillating magnetic field with certain desired characteristics.

In the example of FIG. 1, the computing device 102 includes a peripheral interface 150 and a user interface 152, in addition to the one or more processors 112 and the memory 114. The peripheral interface 152 can be Serial Peripheral Interface (SPI), a Universal Serial Bus (USB), or any suitable wireless interface such as Wireless Personal Area Network (WPAN) interface (e.g., Bluetooth®), a Wireless Local Area Network (WLAN) interface (e.g., Wi-Fi®), etc. The computing device 102 can use the peripheral interface 150 to transmit commands to the microstimulators 104. More particularly, the computing device 102 in the example implementation of FIG. 1 provides commands to the microstimulators 104 via the peripheral interface 150 and a control circuitry 154 of the stimulator support platform 106.

The control circuitry 154 can be configured to receive commands for the individual microstimulators 104-1, 104-02, etc. and turn on or off the motors in the microstimulators 104-1, 104-02, etc., vary the speed of rotation or other type of oscillation in the motors, etc. The control circuitry 154 thus can operate as a demultiplexer. Further, as indicated above, in some implementations the controlling hardware 110 is embedded in the stimulator support platform 106, and thus the entire control functionality of the system 100 can be provided in the control circuitry 154. More generally, control functionality of the system 100, such as the control logic for activating the microstimulators 104 in accordance with various stimulation patterns, can be distributed between the computing device 102 and the control circuitry 154 in any suitable manner, including providing the entire control functionality entirely in the computing device 102 or entirely in the control circuitry 154.

The user interface 152 can include a touchscreen configured to receive input and display output or separate input (e.g., a keyboard, a pointing device) and output (e.g., a display) components. An operator can use the user interface 152 to provide commands to select the desired particular stimulation parameters 122 for a particular microstimulator or a stimulation pattern that includes multiple stimulation parameters 122 for the respective microstimulators. Further, the system 100 in some implementations can include one or more magnetic sensors such as microelectromechanical system (MEMS) sensors, and the user device 102 can provide readings from these magnetic sensors via the user interface 152.

The microstimulator platform 106 can be a harness, a helmet, a brace, etc. Further, the microstimulator platform 106 can be a part of a hospital bed, and the system 100 in some cases can apply stimulation to a sleeping subject. Still further, the microstimulator platform 106 in some implementations can be an intraoperative probe which a clinician can guide manually. In some implementations, the microstimulator platform 106 includes one or more magnetic sensors to provide sensor readings to the operator as discussed above and/or provide a feedback signal to the controlling hardware 110, so that the controlling hardware 110 can tune certain operational parameters to achieve the desired strength of the magnetic field.

The microstimulator platform 106 in some implementations can include a power storage device, such as a battery, to power the microstimulators 104. In other implementations, the computing device 102 can be configured to provide electric power to the microstimulator platform 106 via the peripheral interface 150.

The system 100 in various scenarios can generate stimulation sessions that are intermittent or continuous, ranging in duration from 1 minute to 18 hours for a given therapy session, depending on the amount of desired stimulation determined by a treatment plan. The frequency of each oscillatory stimulus, and therefore the oscillatory motion of the motor, can range from 5 Hertz to 400 Hertz. The microstimulators 104 can provide oscillatory stimulus as one or more pulses in a series. In some example implementations, the pulse lengths range from 10 milliseconds to 5 seconds, with inter-stimulus pulse intervals ranging from 10 milliseconds to 10 minutes, resulting in pulse train duty cycles ranging from 0.001% to 50%. The oscillatory frequency, timing, pulse duration, and inter-stimulus pulse interval of the oscillatory stimulus any of the microstimulators 104 provide may be kept the same, varied in groups, and/or varied independently for each microstimulators 104. The oscillatory stimulus pulses may vary in temporal length and inter-stimulus pulse interval from pulse to pulse as required to provide adequate field intensity to a target site or volume. The stimulus pulses may have amplitude envelopes whose shapes are square, Gaussian, sinusoidal, ramp, sawtooth, etc., to provide adequate field amplitude to a target site or volume. Additionally, the system 100 can ramp the oscillatory frequency up and/or down to maximum desired frequencies or between frequencies for a given therapeutic session.

In some implementations, the controlling hardware 110 can activate the microstimulators 104 one at a time, simultaneously, sequentially, in-pairs, in groups, or according to any combination thereof (e.g. sequentially in pairs, one group at a time). In fact, the controlling hardware 110 can activate any number of microstimulators 104 in any sequence able to deliver the desired OMF to a target site or volume.

The controlling hardware 110 in some cases can implement a beat frequency stimulation when generating OMF in a target site or volume. According to the beat frequency stimulation approach, the controlling hardware 110 causes the magnets in two microstimulators to oscillate at different frequencies so as to produce a beat frequency at a target site or volume. For example, the microstimulator 104-1 can oscillate at 320 Hz, while the microstimulator 104-2 can oscillate at 400 Hz. Due to electromagnetic interference, the microstimulator 104-1 and 104-2 generate a beat frequency of 80 Hz (which is the difference between the frequencies of 320 Hz and 400 Hz) at a target site or volume. The amplitude of the OMF at this beat frequency is twice the amplitude of the OMF the microstimulator 104-1 or 104-02 induces independently. The system 100 can implement beat frequency stimulation when high-amplitude low-frequency fields are required or desirable in treatment.

Due to the small dimensions of the magnets and motors in the microstimulators 104, as well as the ability to operate using a battery, the system 100 can be portable. Therefore, treatment may be performed at any time or location. Moreover, the control application 120 can be installed on a smartphone, a tablet computer, or a portable computer device as discussed above.

As discussed above, the control application 120 can operate according to the stimulation parameters 122 and various stimulation patterns or preprogrammed therapy sessions. The control application 120 additionally can implement safety features such as limiting the amount of treatment a patient can receive daily, weekly, or monthly, limiting how often or when a patient can apply treatment (e.g., only on weekdays, only on a specific day of the week, only for a period of four weeks).

Next, the mechanisms by which the system 100 causes apoptosis in certain cells of the tissue 140, and certain test results produced when the system 100 in one example implementation operated on certain samples, are discussed with reference to FIGS. 2-8.

Figure 2:
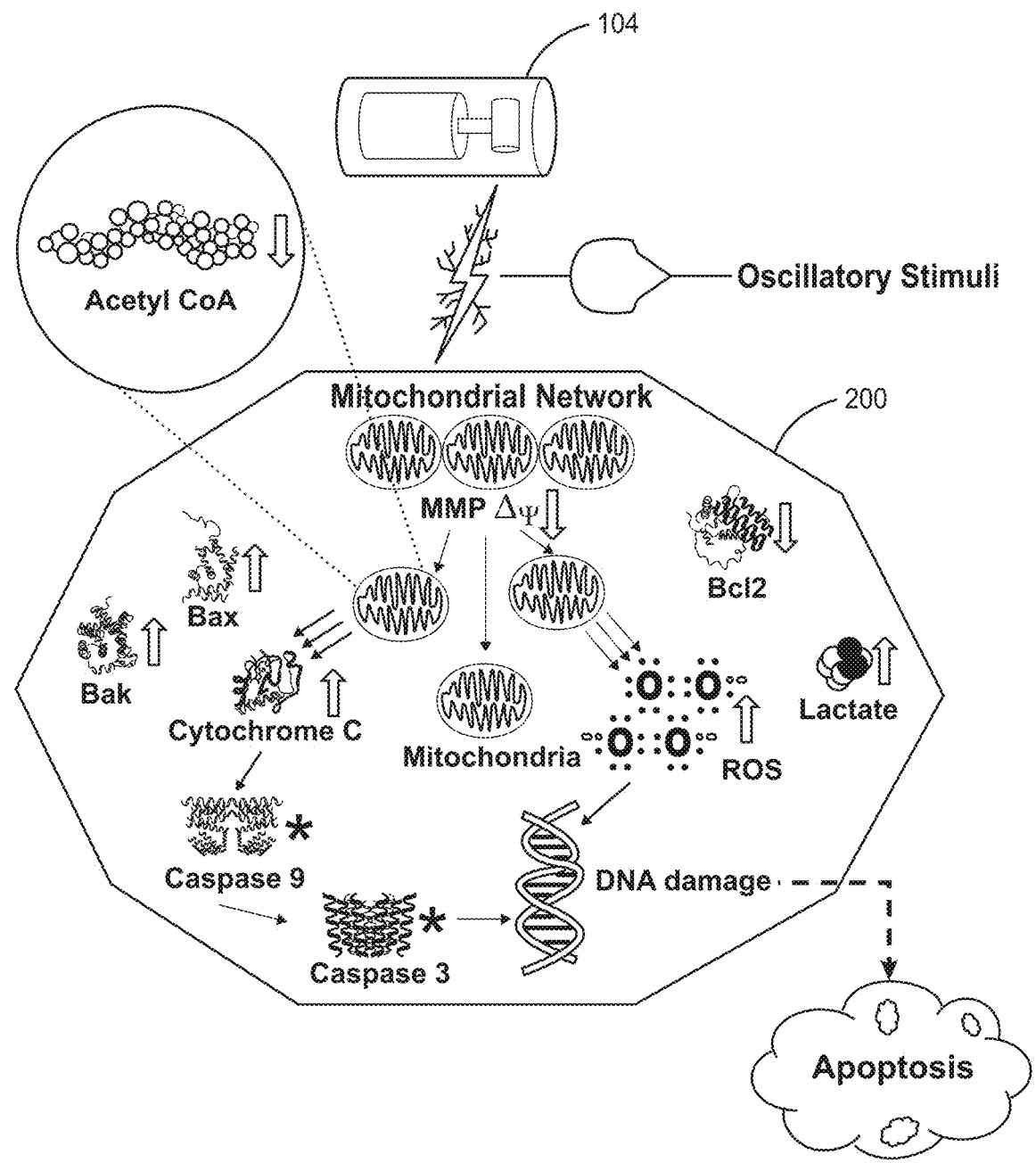
FIG. 2 schematically illustrates the interaction between the system of FIG. 1 and mitochondrial function of a cell.

FIG. 2 schematically illustrates interaction between the system 100, here represented by an example microstimulator 104, and mitochondrial function of an example GBM cell 200. The microstimulator 104 (or several such microstimulators, as discussed above) generates OMFs that decrease mitochondrial glucose oxidation in the tricarboxylic acid (TCA) cycle (or "Krebs cycle") via the production of [1,2-$^{13}$C]acetyl-CoA, increase metabolic flux of glycolysis (determined via $^{13}$C enrichment of lactate from $^1$H NMR spectrum of the cell extracts), disrupts electron flow in the ETC, increases superoxide, peroxide, and other reactive oxygen species generation, opens the MPTP and activates caspase-3-mediated or an alternate apoptotic pathway in GBM cells.

In particular, the system 100 causes one or more stimulators 104 to generate a rapidly changing magnetic field, which in turn disrupts electron flow in the cells 200 present in the tissue exposed to the magnetic field. As schematically illustrated in FIG. 2, the system 100 creates electrical perturbation of mitochondria, which are intracellular energy-producing components, and generates localized release of harmful chemicals (reactive oxygen species and cytochrome C) within cells with impaired mitochondrial function including, but not limited to, cancer cells. This localized release of harmful chemicals triggers apoptosis, or a molecular cell death process.

More particularly, cancer cells demand more energy in the form of adenosine triphosphate (ATP) produced by mitochondria due to uncontrolled cell divisions, and thus are under heightened stress. The system generates the OMF which in turn produces rapidly fluctuating or sustained depolarizations of the mitochondrial membrane potential (MMP) in the tissue. This process leads to fragmentation of mitochondrial networks and disruption of ATP generating proton flux/electron transport in individual mitochondria. Further, this process cases leakage of cytochrome C and reactive oxygen species (ROS) which depolarize the MMP further and cause degradation of mitochondria. These events collectively trigger the molecular pathway that leads to DNA damage and apoptosis in the cancer cells. Because normal cells (e.g., healthy cells) have a larger amount of mitochondria, have lower demand for ATP, and are not under stress, disruption of electron flow and small amount of ROS formation and MMP depolarization does not trigger apoptosis in normal cells. The lack of apoptosis might also be due to triggering of antioxidant mechanisms that counteract ROS increase.

During several tests discussed below, the system 100 in one implementation generated oscillating magnetic fields which, when applied to GBM cells, caused the breakdown of mitochondrial networks, disintegration of mitochondria due to MMP depolarization, and a decrease in Krebs cycle metabolites. The system 100 in this implementation included a single microstimulator with a neodymium magnet magnetized at 1.48 Tesla. The motor rotated the magnet at approximately 350 Hz. The system 100 generated stimulus pulses of approximately 500 ms duration, with an inter-stimulus interval of 1000 ms (as measured from the beginning of one pulse to the beginning of the next pulse). The microstimulator was placed at a distance of approximately 1 cm from the cells in a slide chamber. Intermittent stimulation with these 500 ms pulses, separated by 1000 ms, was conducted for 60 to 90 minutes.

In some embodiments, the microstimulators 104 oscillate at frequencies in the range of 250 to 350 HZ, to generate OMFs with frequencies of 250-350 Hz. In some cases, the frequencies at which the microstimulators 104 oscillate include subharmonic and superharmonic frequencies. The system 100 can apply OMFs as approximately 250 millisecond pulses with a 50 percent duty cycle (i.e., with an approximately 250 ms ON subcycle or pulse length followed by an approximately 250 ms OFF subcycle or inter-stimulus pulse interval), for example. The system 100 can nest these pulses (or other suitable pulses) in a supercycle that includes an ON period $P_{ON}$ followed by an OFF period $P_{OFF}$. In some implementations, $P_{ON}$ lasts between 5 and 900 seconds, and $P_{OFF}$ lasts between 1 and 300 seconds. Additionally, the system 100 can ramp up the OMF frequency may be ramped up over a 75 to 100 millisecond period to a peak frequency, and subsequently ramped the OMF frequency down from the peak frequency over a 250 millisecond period.

Mitochondria in the experiments outlined below were stained with MitoTracker® and MitoSox® dyes. During repetitive stimulation and real-time imaging of live GBM cells over 10 and 90 minutes, and in fixed cells after 3 hours of stimulation, the fluorescence of these dyes changed, confirming the breakdown of mitochondrial networks, disintegration of mitochondria due to MMP depolarization, and a decrease in Krebs cycle metabolites due to the system 100 generating OMFs. Further, a decrease of approximately 10% in mitochondrial acetyl-CoA formation, combined with a similar increase in lactate (a byproduct of glycolysis in the cytoplasm) was observed using nuclear magnetic resonance spectroscopy.

Figure 3A:
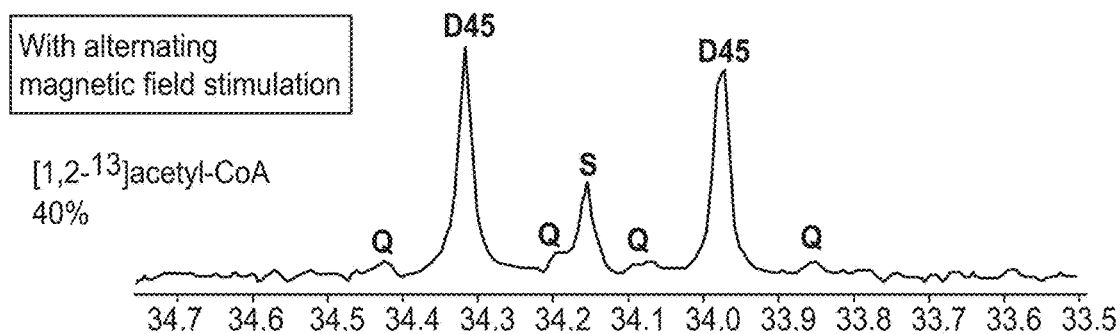
FIGS. 3A and 3B illustrate a $^{13}$C-NMR spectrum of glutamate in a sample of GBM cells to which the system of FIG. 1 applied oscillating magnetic fields (OMFs) for a certain of time, and the $^{13}$C-NMR spectrum of glutamate in a corresponding control sample.
Figure 3B:
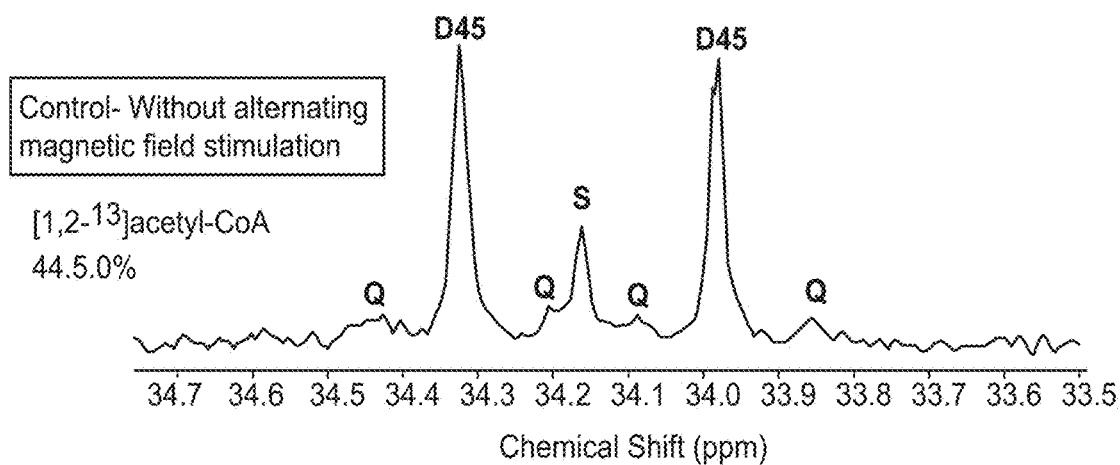

More particularly, FIGS. 3A and 3B illustrate a $^{13}$C-NMR spectrum of glutamate in GBM cells for two samples. In the first instance illustrated in FIG. 3A, the system 100 disrupted electron flow through an oscillating magnetic field in the first sample for three hours. In the second (control) instance illustrated in FIG. 3B, the second sample was not exposed to OMF. As illustrated in FIGS. 3A and 3B, the OMFs generated by the system 100 decreased the synthesis of glucose-derived 13C-acetyl-CoA.

Figure 4A:
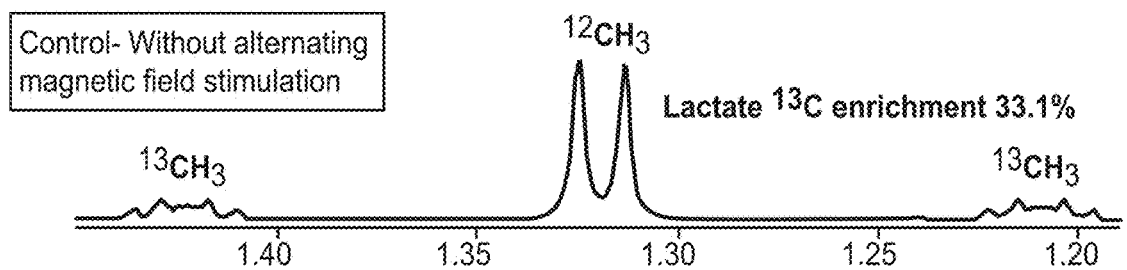
FIGS. 4A and 4B illustrate a $^{1}$H-NMR spectrum of methyl protons of lactate in a sample of GBM cells to which the system of FIG. 1 applied OMF for a certain of time, and the $^{1}$H-NMR spectrum of methyl protons of lactate in a corresponding control sample.
Figure 4B:
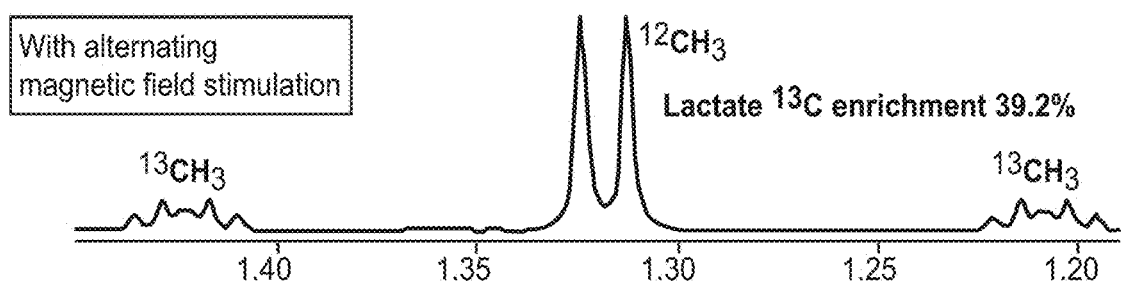

FIGS. 4A and 4B illustrate an $^1$H-NMR spectrum of methyl protons of lactate in GBM cells for two samples. $^{13}$C satellite signals here arise from 13C-1H J-coupling. In the first (control) instance illustrated in FIG. 4A, the first sample was not exposed to OMF generated by the system 100. In the second instance of FIG. 4B, the system 100 generated OMFs in the second sample for three hours, using an oscillating magnetic field. As illustrated in FIG. 4D, the OMFs increased glycolytic flux, which in turn lead to an increased level of 13C enrichment in the tumor lactate pool.

Figure 5:
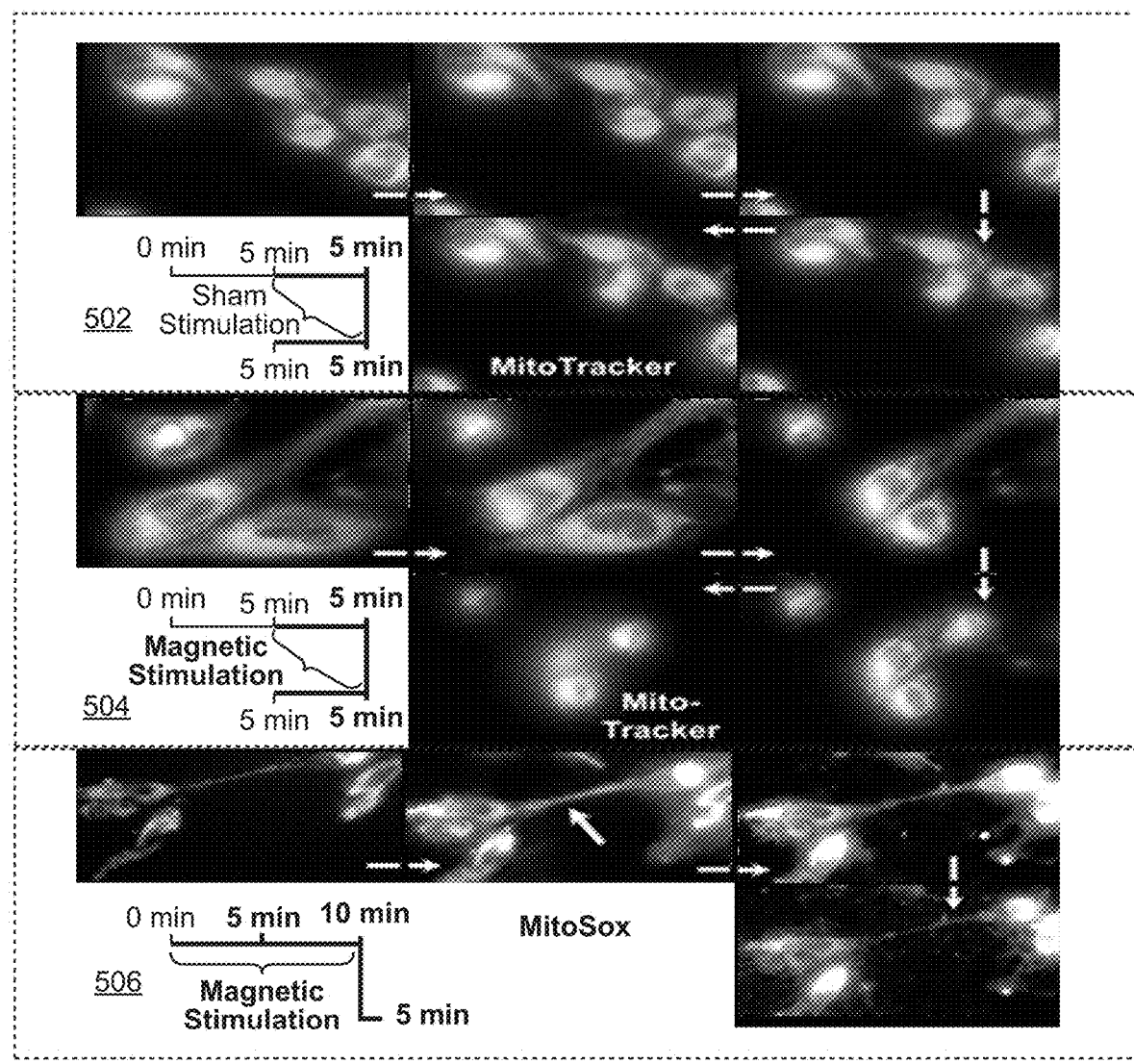
FIG. 5 illustrates changes in the morphology of mitochondrial networks in GBM cells in response to the OMF which the system of FIG. 1 generated.

FIG. 5 illustrates changes in the morphology of mitochondrial networks in GBM cells in response to a rotating magnetic field, which the system 100 generated. In the experiments of FIG. 5, a mitochondrial membrane potential probe, MitoTracker®, was used in labeling.

The cells in sample 502 went through sham-stimulation and manifested almost no changes. However, when the system applied 100 a rotating magnetic field to sample 504, fission of mitochondrial networks was observed. After 10 minutes of stimulation, almost no mitochondrial networks or structured clusters were observable.

In sample 506, cells were preloaded with a mitochondrial superoxide probe, MitoSox®, and were subjected to 10 minutes of magnetic stimulation. In the long thin cytosolic strand between the cells, extremely bright mitochondria were seen within a long-range network (arrow second panel). However, after 10 minutes of stimulation, the network is observed to undergo complete dissipation, with no recovery after 5 minutes, post stimulation.

Figure 6A:
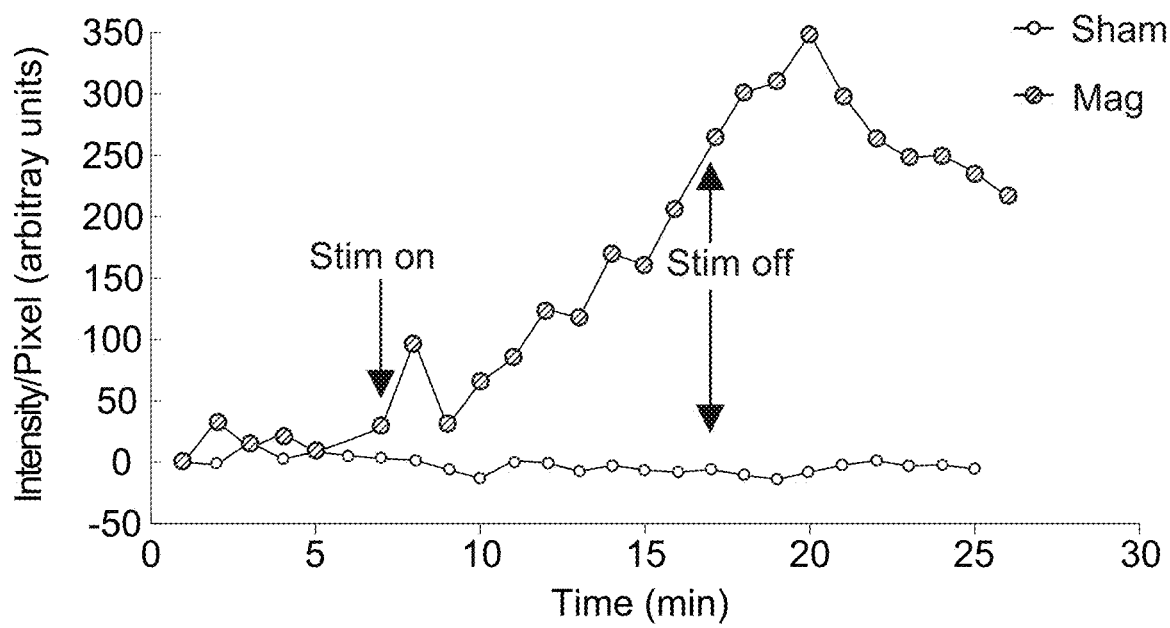
FIGS. 6A and 6B illustrate increased release of the superoxide component of reactive oxygen (ROS) species in response to the OMF generated by the system of FIG. 1.
Figure 6B:
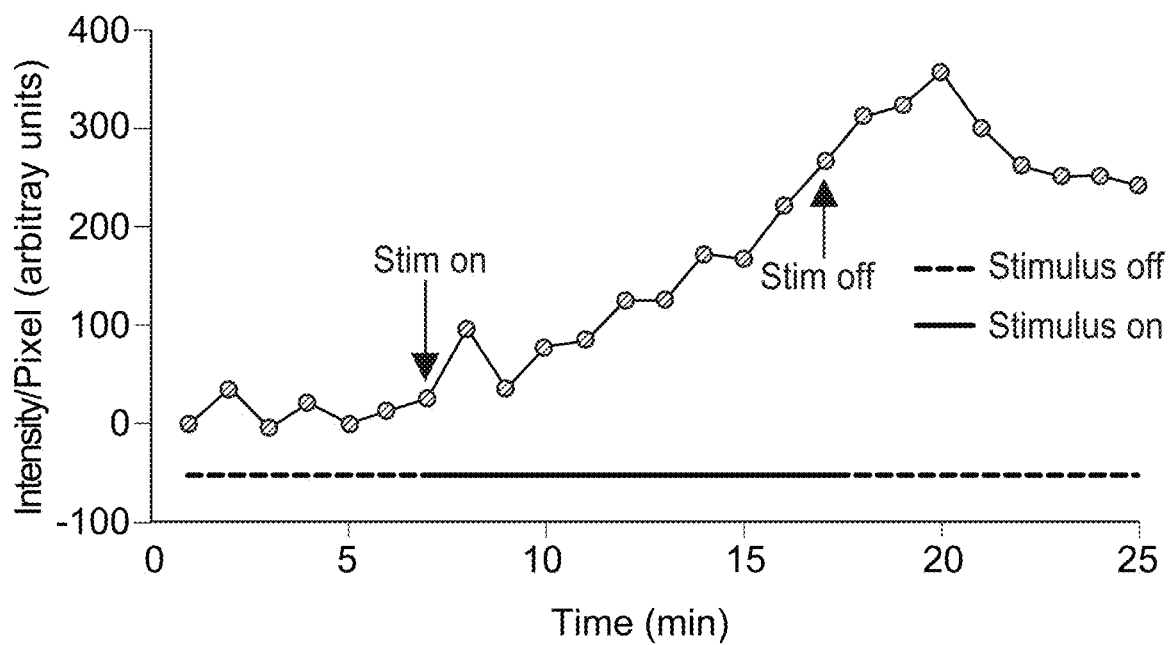

Next, FIGS. 6A and 6B illustrate increased release of the superoxide component of reactive oxygen species in response to a rotating magnetic field generated by the system 100. FIG. 6A illustrates measurements of fluorescence of MitoSox stain for superoxide at different points in time, in relation to activating magnetic or sham stimulation. FIG. 6B illustrates the difference between magnetic and sham stimulation, revealing an increase in superoxide levels in GBM cells following application of stimulation and decrease in superoxide levels in GBM cells following deactivation of the stimulus.

Figure 7A:
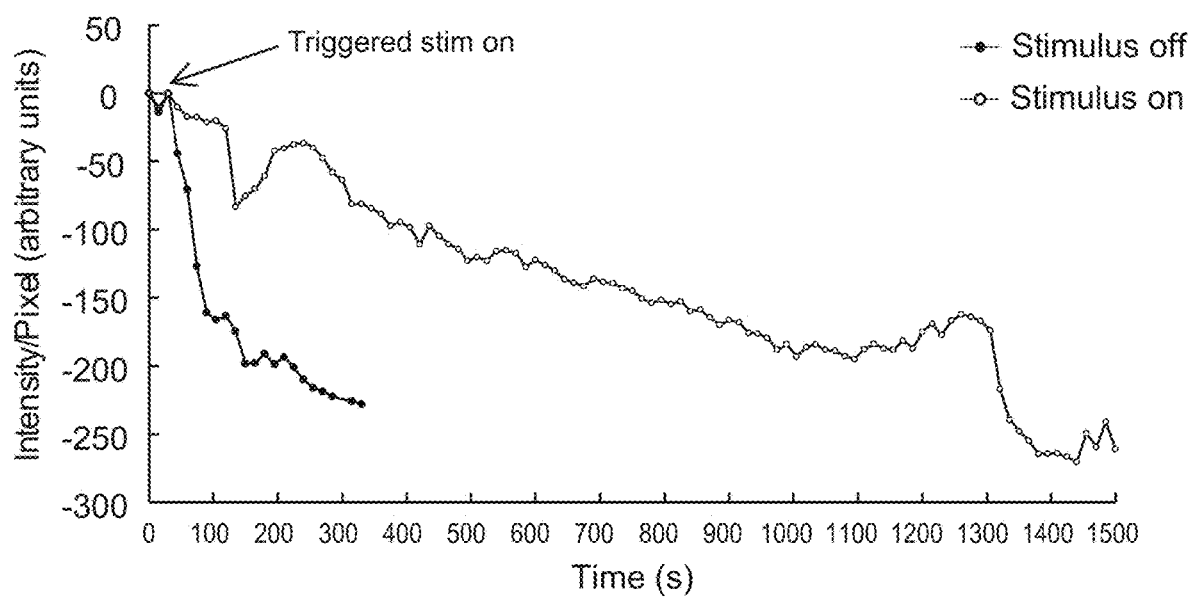
FIGS. 7A and 7B illustrate increase release of the peroxide component of ROS in response to the OMF generated by the system of FIG. 1.
Figure 7B:
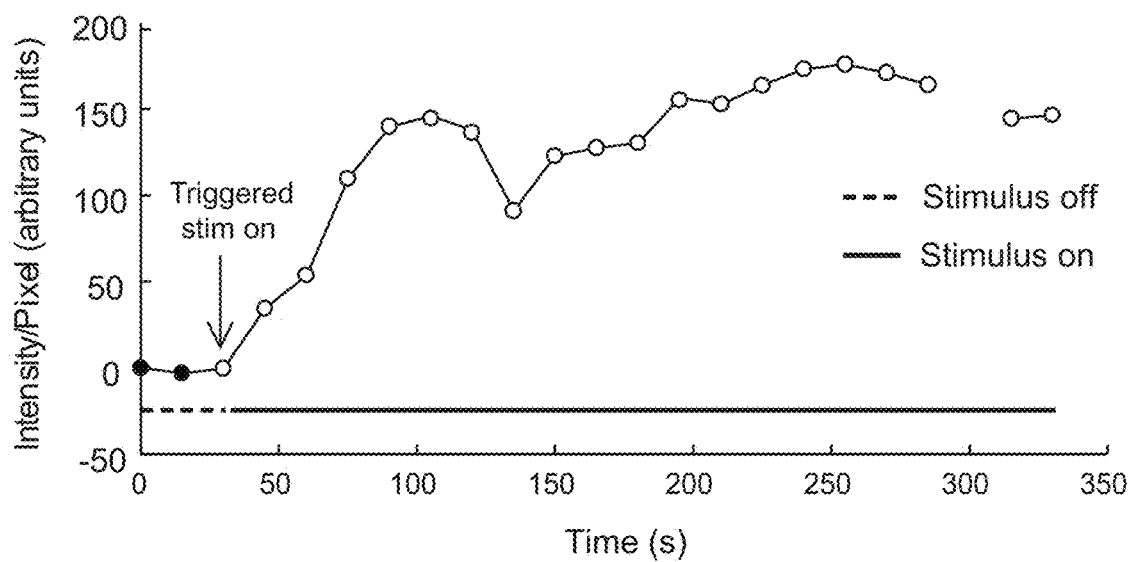

FIGS. 7A and 7B illustrate an increased release of the peroxide component of reactive oxygen specifies in response to a rotating magnetic field generated by the system 100. The graph of FIG. 7A illustrates the fluorescence of an $H_2$DCF-AM probe for peroxide measured at different points in time. To rule out any effects of a static magnetic field, here magnetic stimulation triggered the system 100 rotating the magnet is compared to the magnet being static. The graph of FIG. 7B illustrates the difference in fluorescence between "stimulus on" and "stimulus off" states, revealing an increase in peroxide levels in GBM cells following stimulation by the system 100 using a rotating magnet.

Figure 8:
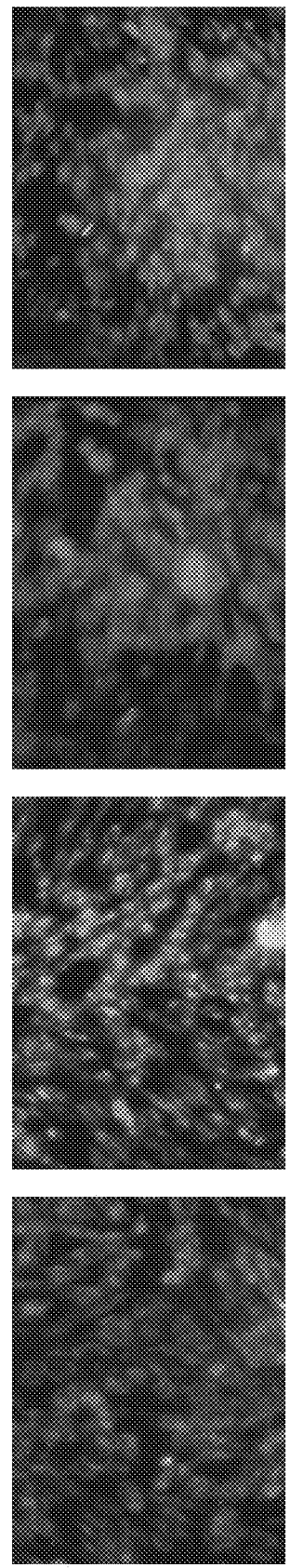
FIG. 8 illustrates increased level of Caspace-3 Activity in response to the to the OMF generated by the system of FIG. 1.

FIG. 8 illustrates an increase in the level of Caspase-3 Activity in response to the OMFs generated by the system 100. In particular, FIG. 8 illustrates that treatment with an oscillating (e.g., rotating) magnetic field causes progressive increase in staining for caspace-3 in GBM cells. The four panels in FIG. 8 illustrate a sample of GBM cells before treatment, after 10 minutes, 20 minutes of treatment, and 30 minutes of treatment. Each successive panel displays a greater amount of green staining for caspace-3, reflecting an increase in the level of activity of this enzyme, which is a final step in the apoptotic pathway. As set out above, the techniques described in this disclosure can apply to various cells having mitochondrial impairment, and are not solely applicable only to cancer cells. Although the examples are drawn to GBM cells, it is expected that the systems and methods described herein are applicable to all types of cancer cells, including other brain cancer cells, carcinomas of the pancreas, breast, lung, colon, ovary, and other cancer cells within other parts of the body of a subject. Additionally, magnetic fields penetrate all magnetically inert materials and tissues equally and therefore, OMF may be used as an effective form of therapy for tumors deep within body structures.

Example Application of OMF in Conjunction with a Chemical Agent

In embodiments and implementations of the oncomagnetic therapy methods and systems described herein, oncomagnetic therapy may be performed in conjunction with the administration of other chemicals, drugs, or radiations to complement the oncomagnetic therapy. In embodiments, a ketone body, or acetate, or free fatty acid (octanoate or palmitate) may be provided to a region of tissue or cell, tumor, or cancer cells in addition to the oncomagnetic therapy to complement the oncomagnetic therapy. For example, there is evidence that β-hydroxybutyrate (BHB) a well-known ketone body component of the low-carb ketogenic diet, or octanoate or palmitate, commonly found free fatty acids in the circulation, potentiates the anti-cancer effects of OMF. Therefore, embodiments are envisioned that combine the administration of BHB, or acetate, or free fatty acid and OMF as a more effective treatment of cancer compared to OMF alone. It is envisioned that other bodies, chemicals, or treatments may be applied in addition to oncomagnetic therapy to provide treatment to a region of tissue, tumor, or cancer cells.

Descriptions and Examples of Microstimulators

Next, several example implementations of a microstimulator that can operate in the system of FIG. 1, and example implementations of a support platform on which these microstimulator can be mounted, are discussed with reference to FIGS. 9-13.

Figure 9:
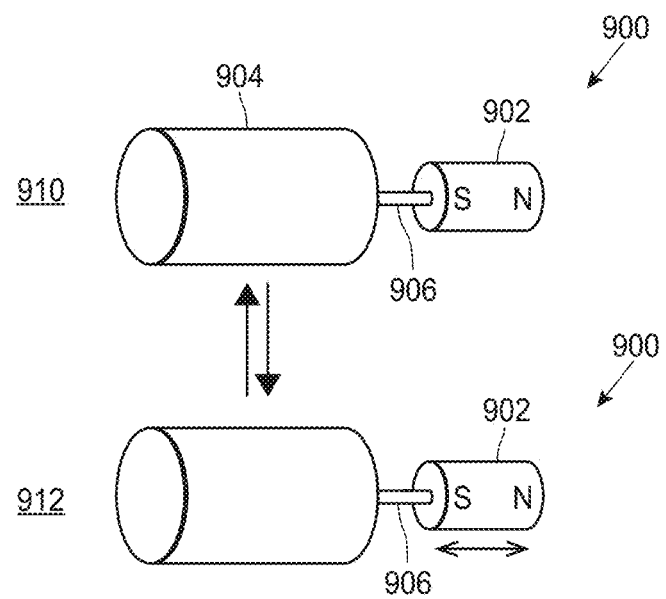
FIG. 9 illustrates a microstimulator that can operate in the system of FIG. 1, according to one example implementation.

Referring first to FIG. 9, an example microstimulator 900 can operate in the system of FIG. 1 as a microstimulator 134-1, 134-2, . . . 134-N. The microstimulator 900 may include a magnet 902 and an electric motor 904. The motor 904 controls motion and position of the magnet 902. The magnet 902 can be affixed to a drive shaft 906 of the motor 904 to allow the motor 904 to oscillate the magnet 902. In this example implementation, oscillation of the magnet 902 includes translation of the magnet along the axis of the drive shaft 906.

FIG. 9 illustrates the stimulator 900 in two operational states: in top half of the figure, the magnet 902 in resting position, with the motor 704 not oscillating the magnet 902; in the bottom half of the figure, the motor 904 is active and oscillates the magnet 902, thereby generating an oscillating, rapidly changing magnetic field about the magnet.

The magnet 902 may have dimensions on the order of centimeters. For example, the magnet 902 can be a cylindrical magnet that is less than one centimeter long, and less than a half a centimeter in diameter. In various implementations, the magnet 902 may be shaped as a disc, a cylinder, a block, a ring, a sphere, or any other suitable solid.

The magnet 902 in various implementations can be permanent magnet, such as a rare earth permanent magnet, a ferrite magnet, an alnico magnet, or any other type of compact magnet. When the magnet 902 is a rare earth magnet, the magnet 902 can be a neodymium magnet, a samarium-cobalt magnet, or a magnetostrictive magnet, as these types of magnets have strong magnetic fields, typically greater than 1.2 Tesla. In other implementations, the magnet 902 may be a small electromagnet, when the requisite high-strength magnetic field as well as the appropriate amount of cooling to prevent heating and melting of the magnet coils can be achieved.

Further, the magnet 902 can be magnetized through thickness, axially, diametrically, north on the outside face, south on the outside face, through circumference, or using any other magnetization polarization. The specific shape and magnetization may determine the position and orientation of the magnet in relation to the desired treatment region or target site, which in turn may determine the type of motor and motion applied to the magnet.

The motor 904 can be a high-speed motor operating at 19,000 RPM or more, for example. The motor 904 of FIG. 9 is a oscillates the magnet translationally, in other embodiments the motor 904 may rotate the magnet 902. The magnet 902 can be a permanent magnet, such that rotation of the magnet 902 produces a rapidly changing magnetic field. Further, the motor 902 can be a variable-speed motor capable of oscillating the magnet 902 faster or slower to adjust the amplitude of the OMF at a target site or volume. More generally, the motor 904 can be a linear DC solenoid, a rotary solenoid, a push-pull solenoid, any brush or brushless motor, or any other kind of compact motor. The motor 904 can require a voltage of 3-12 volts and a current on the order of hundreds of milliamps to operate. Further, the motor 904 can be sufficiently small so that one or more motors 904 can be mounted on the support platform 106 implemented as a wearable cap, a belt, or a brace structure to be worn by or affixed to a subject, a frame attached to parts of a bed, chair, etc.

Figure 10:
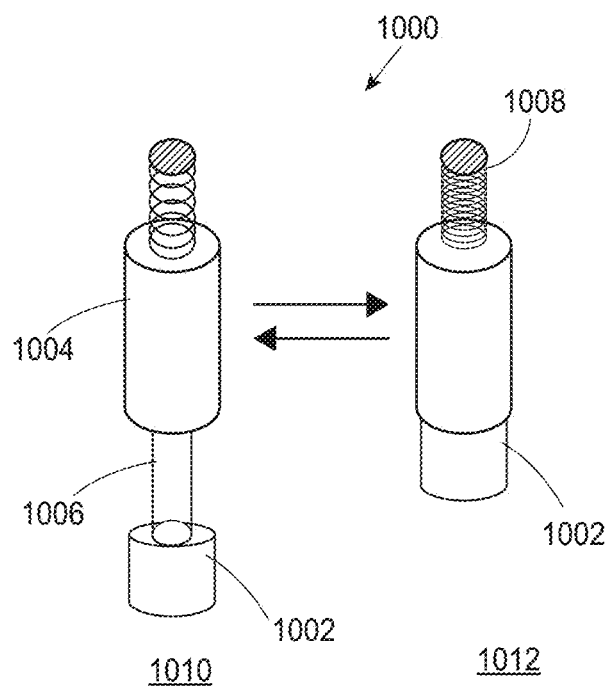
FIG. 10 illustrates another microstimulator that can operate in the system of FIG. 1, according to one example implementation.

FIG. 10 illustrates another example embodiment of a microstimulator that can operate in the system 100 of FIG. 1 as a microstimulator 104. The microstimulator 1000 includes a magnet 1002 attached to a rod shaft 1006 of a push/pull electric motor 1004 which can oscillate the magnet 1002 longitudinally rather. The microstimulator 1000 optionally can include a biasing spring 1008 to drive the magnet 1002 in the direction opposite to that communicated by the motor 1004. The magnet 1002 can be a permanent magnet similar to the magnet 902 discussed above. The push/pull electric motor 1004 can oscillate the magnet 1002 at 19,000 RPM, for example, to generate a rapidly changing magnetic field. For clarity, the microstimulator 1000 is illustrated in two operational states between the microstimulator 1000 transitions, state 1010 (in which the magnet 1002 is in the extended position relative to the motor 1004), and state 1012 (in which the magnet 1002 is in the compressed position relative to the motor 1004).

The two embodiments 900 and 1000 of FIGS. 9 and 10 are non-encompassing and are provided clarity. Accordingly, it will be understood that any other motor and magnet configuration also may be used to alter electron flow through an oscillating magnetic field.

The microstimulators 900, 1000 may be attached to the support platform 106 that can be a wearable apparatus such as a cap, helmet, belt, brace, etc. The support platform 106 also can be implemented as a portable grid, and the microstimulators 900, 1000 can be attached to the grid according to various configurations. The microstimulators 900, 1000 may be attached to such platform by means of hook and loop mechanisms, latching mechanisms, buttons or snaps, adhesive tapes, soluble adhesives, elastic pockets or cushions, or any other suitable attachment mechanism. The support platform 106 can be made of cloth or soft plastic, hard plastic, metal, or any other material for positioning the microstimulators 900, 1000 at desired locations in relation to a target site or volume. The microstimulators 900, 1000 also may also be integrated into the end of an intraoperative probe, as discussed above.

Descriptions and Examples of OMF Apparatus

Figure 11:
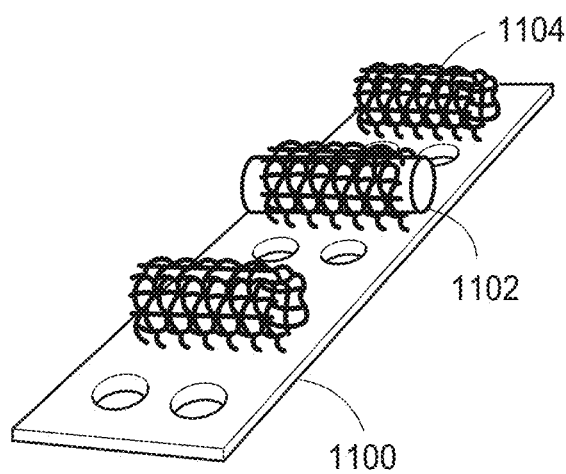
FIG. 11 illustrates an example flexible strap on which one or several microstimulators of FIG. 9 or 10 can be mounted.
Figure 12:
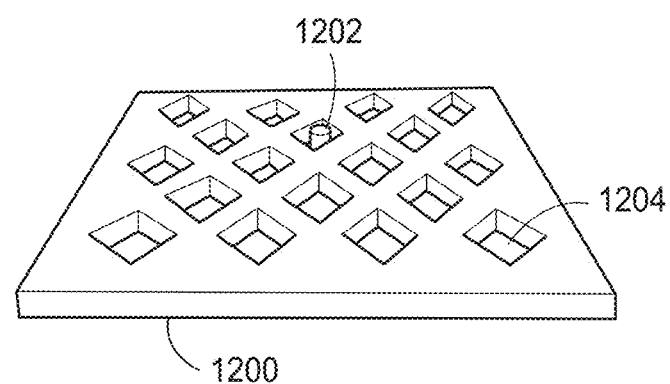
FIG. 12 illustrates an example insert on which one or several microstimulators of FIG. 9 or 10 can be mounted.
Figure 13:
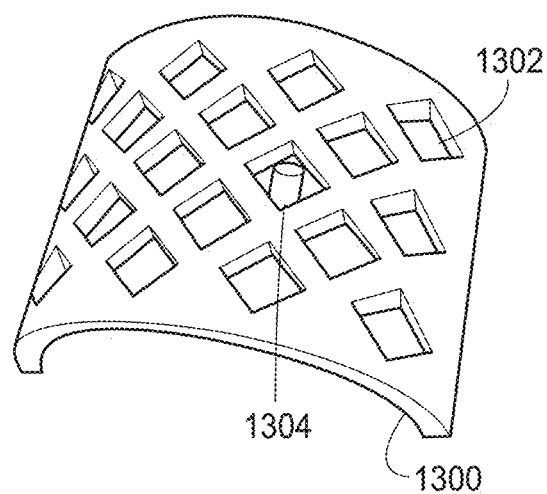
FIG. 13 illustrates an example frame on which one or several microstimulators of FIG. 9 or 10 can be mounted.

FIGS. 11-13 illustrate three example implementations of the support platform 106 that may house or position microstimulators. In particular, FIG. 11 illustrates a flexible strap 1100 with a microstimulator 1102 inserted into a pocket 1104. The flexible strap 1100 may be integrated into a helmet, brace, belt, or other wearable apparatus or any apparatus to position the microstimulator 1102 at a desired position relative to a patient. FIG. 12 illustrates a flat plastic insert 1200 with an attached microstimulator 1202 placed inside cushions 1204. FIG. 13 illustrates a curved, light, non-magnetic metal or plastic frame 1300 with an attached microstimulator 1304 integrated into bridge frames or brackets 1302. The microstimulators 1102, 1202, and 1304 can be implemented as the microstimulator 900, 1000, or another suitable type of a microstimulator.

In general, the support platforms 1100, 1200, and 13003 can support any number of microstimulators may be attached to any apparatus able to position the microstimulators at desired positions relative to a patient, that enable the delivery of a magnetic field to a target site or volume.

Referring to FIGS. 11-13, one or multiple microstimulators can be fixed in place near and/or surrounding the target volume of tissue to be treated. In the implementations with multiple microstimulators, any two fixed microstimulators can be separated from each other by at least 2 cm at their magnet ends. Also, in their fixed positions, the long axes of the microstimulators can be oriented at least at a 60 degree angle with respect to each other. Implementations with multiple microstimulators may enable treatment of larger target volumes and/or simultaneous treatment to multiple target sites or volume.

In another implementation, a single microstimulator, a pair of microstimulators, or an array of microstimulators can be mounted on a grid that can slide, swing or rotate into different positions on near and/or surrounding the target volume of tissue to be treated, in accordance with a programmed scanning protocol. Such an embodiment would allow for multiple target volumes to be treated in one session without having to detach and reattach microstimulators, and/or remove the wearable apparatus.

Examples of Performing OMF Treatment on GBM Cells

The following discussion pertains to one example application of the disclosed apparatus and methods, but is not intended to limit the scope of any of the claims thereto.

In an example application, patient-derived GBM (BT-175) cells were grown in high glucose (25 mM) Dulbecco's modified Eagle's medium (DMEM) supplemented with 20% fetal bovine serum (FBS), 2.0 mM glutamine and 1.0 mM pyruvate at 37° C. under humidified air with 5% CO2. Cells were divided into 2 groups, a test group and a sham group each with n=4. The cells were grown until confluency was reached, ~2.0×106 cells/mL. The cells were starved for glutamine for 24 hour, and the cells were treated with 4.0 mM of [U-$^{13}$C]glutamine (Isotec, Miamisburg, OH) in DMEM (supplemented with 20% FBS, and 1.0 mM pyruvate) for the last three hours of the 24 hours. During the final three hours of the 24 hours, oncoscillators 104, (see FIG. 1), according to embodiments described herein, provided the test group (the tissue 140) with OMF, and the sham group was treated similar to the test group but with rotations of non-magnetic rods of the same dimensions as the magnets in the oncoscillators of the test group. After the oncoscillators 104 applied treatment for three hours, the medium (the tissue 140) was removed by aspiration, the cells were washed with PBS buffer, and the cells were harvested in 50% methanol (1.5 mL/dish). The cells and 50% methanol were transferred to centrifuge tubes, and the contents were snap-frozen in liquid nitrogen. The cells were thawed and frozen twice, then the cells were frozen again and stored at −80° C. after which GC-MS analysis were performed.

The OMF oncoscillators 104 were an assembly of N52 grade neodymium permanent magnets encased in 3D-printed Nylon. Twelve plastic tubes were affixed to a wooden frame by 3D-printed holders. The oncoscillators 104 were positioned in opposite directions and placed 3.7 cm art. The control application 120 executed on a programmable microprocessor-based console 102 on an Android operating system. The console 102 was an electronic tablet computer that controlled the oncooscillators 104 via a Bluetooth connection®. An external battery (9.6V, 2000 mAh) or a 9V power adaptor powered the control console 102. The oncoscillators 104 repeatedly applied the OMF at 200-300 Hz frequencies with on-to-off epochs of 250 or 500 ms duration. The total OMF treatment duration was three hours. The culture plates, with n=4, containing the GBM cells were placed on a plastic plate which was placed on an anti-slip rotating turn table which was mounted on anti-vibration rubber pads. The distance from the base of the plates containing the GBM cells to the center of the oncoscillator magnet was 3.5 cm. The peak to peak amplitude of OMF, at the base of the culture plate, was 3 mT.

Snap-frozen cells were thawed and centrifuged to remove the precipitated proteins and $^{13}$C isotopomer analysis of intracellular metabolites by GC-MS was performed. 50 nmols of standard, sodium 2-oxobutyrate, was added to the cells and the samples were evaporated and derivatized by trimethylsilylation (Tri-Sil HTP, Thermo Scientific). 3 µl of the derivatized solution was injected onto an Agilent 6970 gas chromatograph equipped with a fused silica capillary GC column (30-m length/0.25-mm diameter) and coupled with an Agilent 5973 mass selective detector. Retention times of the metabolites were validated using standards and the measured distributions of carbon isotopomers were corrected for natural abundance of $^{13}$C isotopomer (1.1%).

To observe OMF induced changes in the reductive carboxylation flux of glutamine in the GBM cells, 4 mM of [U-$^{13}$C]glutamine was introduced to the cells during the 3 hours of OMF stimulation. At the end of the 3 hour OMF stimulation, the cells were snap-frozen as described in the methods for GC-MS isotopomer analysis described above. Similarly, a control experiment conducted with sham treatment, instead of OMF, was performed using rotating non-magnetic rods on the sham group.

It was observed that M+5 glutamine metabolized to M+5 α-KG, which was followed by reductive carboxylation generating M+5 citrate through adding a unlabeled carbon by isocitrate dehydrogenease (IDH2) in the TCA cycle, as shown by the model in FIG. 1, illustrating reductive carboxylation of glutamine metabolism. ATP-citrate lyase (ACL) cleaved citrate in the cytosol to produce M+3 OAA/Mal/Asp. Oxidative glutamine metabolism generated M+4 OAA/mal/asp which produced M+4 citrate through the condensation with unlabeled acetyl-CoA. Cleavage of the M+4 citrate in the cytosol by ACL led to the generation of M+2 OAA/mal/asp. Relatively lower levels of M+4 citrate in both cases indicated that the GBM cells rely on the reductive carboxylation of glutamine more than other healthy cells of the same type of tissue.

Figure 14A:
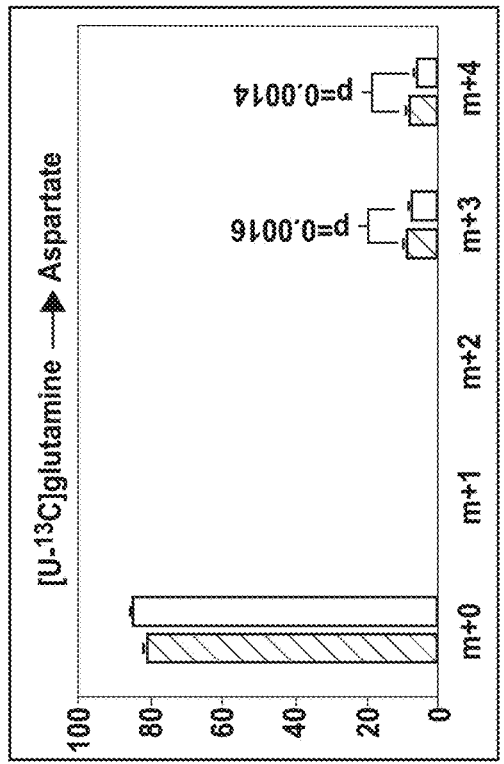
FIGS. 14A through 14D are a set of plots showing mass isotopomer values of various metabolites from GBM cells cultured with [U-$^{13}$C]glutamine with, and without OMF exposure.
Figure 14B:
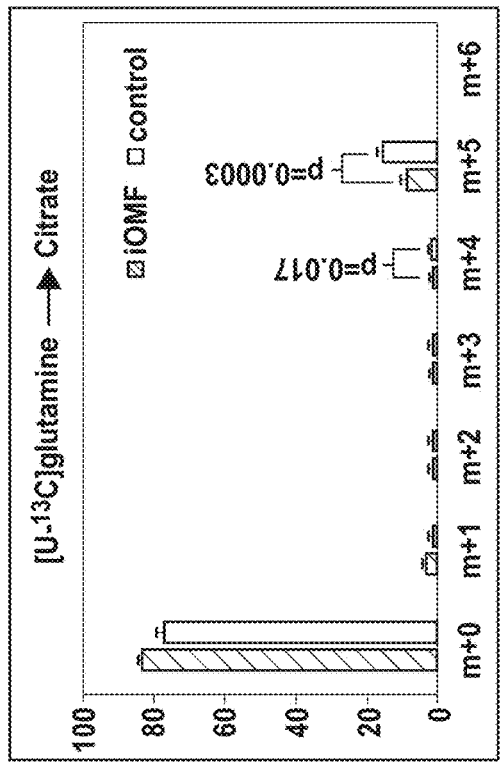
Figure 14C:
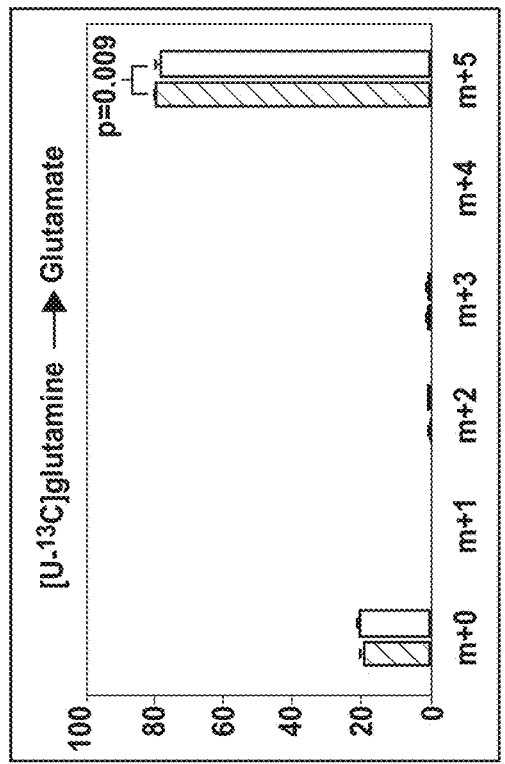
Figure 14D:
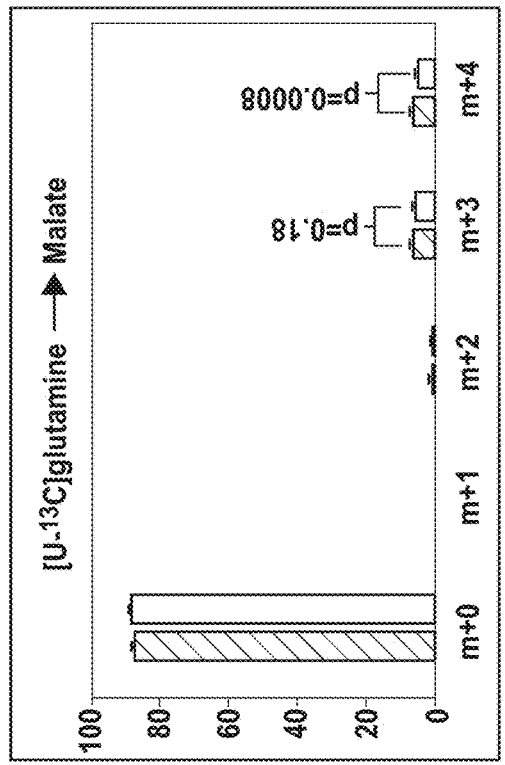

FIG. 14A-14D is a set of plots showing mass isotopomer values of various metabolites from GBM cells cultured with [U-13C]glutamine with, and without OMF exposure. Citrate is shown in FIG. 14A, aspartate is shown in FIG. 14B, malate is shown in FIG. 14C, and glutamate is shown in FIG. 14D. M+5 citrate levels were higher in the GBM cells and the application of OMF reduced the flux through reductive carboxylation pathway, leading 42% less of M+5 citrate isotopomers, compared to control sham-treated GBM cells. The ratio between M5 citrate to M3 malate was 2.42 in the control sham-treated GBM cells, compared to 1.34 in the OM-treated GBM cells, which may be due to the reduced flux through citrate export into cytosol, and cleavage by ACL enzymes due to the application of OMF.

FIG. 14A shows that the OMF exposed GBM cells exhibited a decreased flux through reductive carboxylation of glutamine metabolism. The key enzyme involved in the reductive carboxylation pathway is $NADP^+$/NADPH-dependent IDH1 or IDH2. The mitochondrial $NADPH/NADP^+$ is required to activate reductive carboxylation pathway and silencing either IDH1 (cytosol) or IDH2 (mitochondria) leads to a decrease in the flux through reductive carboxylation pathway.

Figure 15:
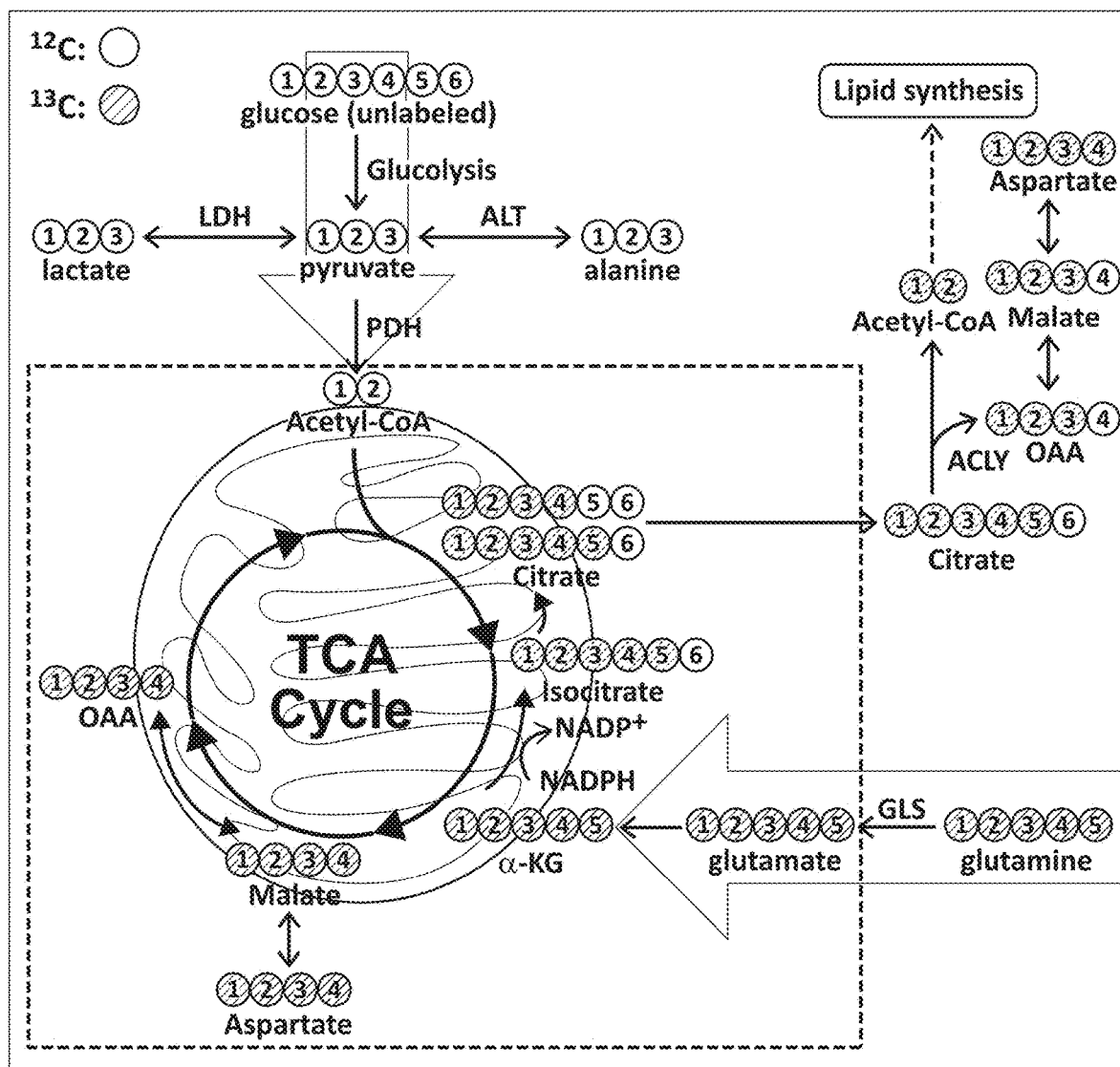
FIG. 15 is a schematic diagram illustrating [U-$^{13}$C] glutamine incubation.

To further explain some of the intracellular effects of applying OMF to a GBM cell, FIG. 15 illustrates details pertaining to the TCA cycle and lipid synthesis in GBM cells. FIG. 15 is a schematic diagram illustrating [U-$^{13}$C] glutamine incubation, an essential process for rapidly dividing cells. 13C labeled glutamine-derived metabolite via reductive carboxylation are used as precursors for lipid synthesis (top right quadrant of FIG. 15). TCA cycle glutamine metabolites are derived from canonical glutamine metabolism, and glucose metabolites are generated through glycolysis from unlabeled glucose metabolism. A decrease in the NADPH-dependent reductive carboxylation flux during the conversion of α-KG to citrate in the TCA cycle (center cycle of FIG. 15) indicate a rapidly fluctuating magnetic field, further resulting in the generation of ROS and causing apoptosis in rapidly dividing cells.

The methods and systems for oncomagnetic therapy described herein for treating GBM cells may disrupt the electron flow in the ETC leading to a shift in the redox potential of $NADPH/NADP^+$. The redox potential shift could decrease the activity of the NADPH-dependent IDH enzyme, causing an attenuation of the glutamine flux through the reductive carboxylation pathway leading to OMF-induced apoptosis of GBM cells.

Figure 16A:
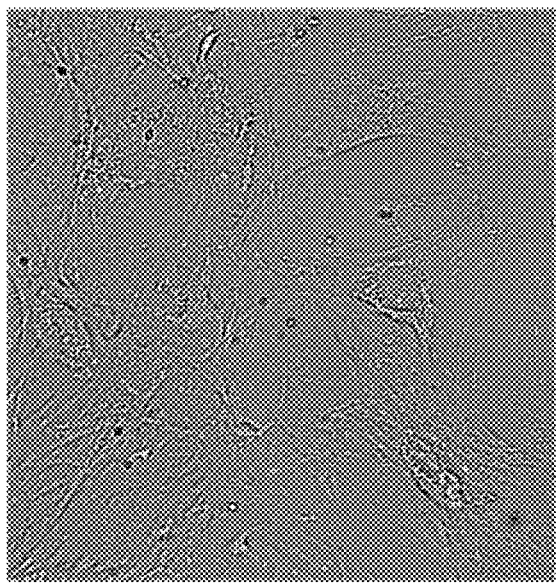
FIGS. 16A and 16B are microscopy images of sham-treated and 01W-treated cells.
Figure 16B:
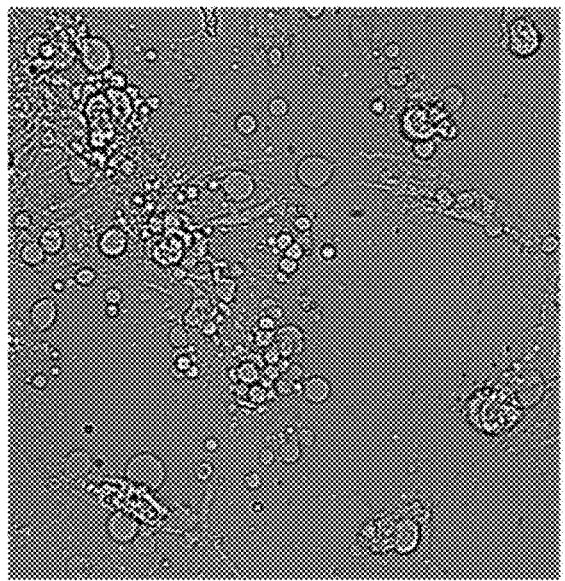

The methods and systems for oncomagnetic therapy described herein for treating GBM cells may disrupt the electron flow in the ETC leading to a shift in the redox potential of $NADPH/NADP^+$. The redox potential shift could decrease the activity of the NADPH-dependent IDH enzyme, causing an attenuation of the glutamine flux through the reductive carboxylation pathway leading to OMF-induced apoptosis of GBM cells. FIGS. 16A and 16B are microscopy images of sham-treated and OMF-treated cells. Blebbing due to cell apoptosis is clearly visible in the OMF-treated cells.

The upregulation of antioxidant mechanisms, such as an increase in glutathione, have also been observed in both cancer, and non-cancer cells undergoing during the application of oncomagnetic therapy as described herein. In the cancerous cells the antioxidants are not enough to prevent the effects of the ROS levels caused by the applied OMF. Non-cancerous cells, such as astrocytes, are protected from oxidative damage due to normal ability and functionality of the cell. Therefore, the upregulation of antioxidant mechanisms due to the application of OMFs further protects non-cancerous cells from any ROS-mediated apoptosis. Further, if normal, non-cancerous cells are exposed to fluorescent light, the cells usually die after about an hour. Due to the upregulation of antioxidant species, normal cells exposed to OMF fields, as described herein, stay alive longer under the exposure to fluorescent light due to the protection from apoptosis caused by singlet oxygen species. Therefore, oncomagnetic therapy may also provide a means for protecting normal cells under certain conditions (e.g., exposure to certain types of radiation such as fluorescent light) in addition to causing apoptosis in cancer cells.

It has also been shown that the methods described herein may cause other types of cells to undergo apoptosis. For example, the methods and systems described herein may be used to kill bacterial cells that do not have mitochondria. In fact, it is envisioned that the methods and systems of applying OMFs described herein may be useful for inducing apoptosis in any cell that utilizes quinones in an energy transport chain or respiratory process.

It should also be understood that while specific frequencies and ranges of frequencies of the OMFs are described herein, other frequencies may be used to target different regions of tissues dependent on the types of tissues and depth of the tissues. Additionally, it should be understood that the harmonic, superharmonic, and subharmonic frequencies of the described frequencies and frequency ranges are envisioned as potential frequencies of the applied OMFs as described herein.

Upon reading this disclosure, those of ordinary skill in the art will appreciate still additional alternative structural and functional designs for disrupting mitochondrial function in cells with mitochondrial impairment through the disclosed principles herein. Thus, while particular embodiments and applications have been illustrated and described, it is to be understood that the disclosed embodiments are not limited to the precise construction and components disclosed herein. Various modifications, changes and variations, which will be apparent to those of ordinary skill in the art, may be made in the arrangement, operation and details of the method and apparatus disclosed herein without departing from the spirit and scope defined in the appended claims.

Descriptions and Examples of a Portable OMF Device

Figure 17:
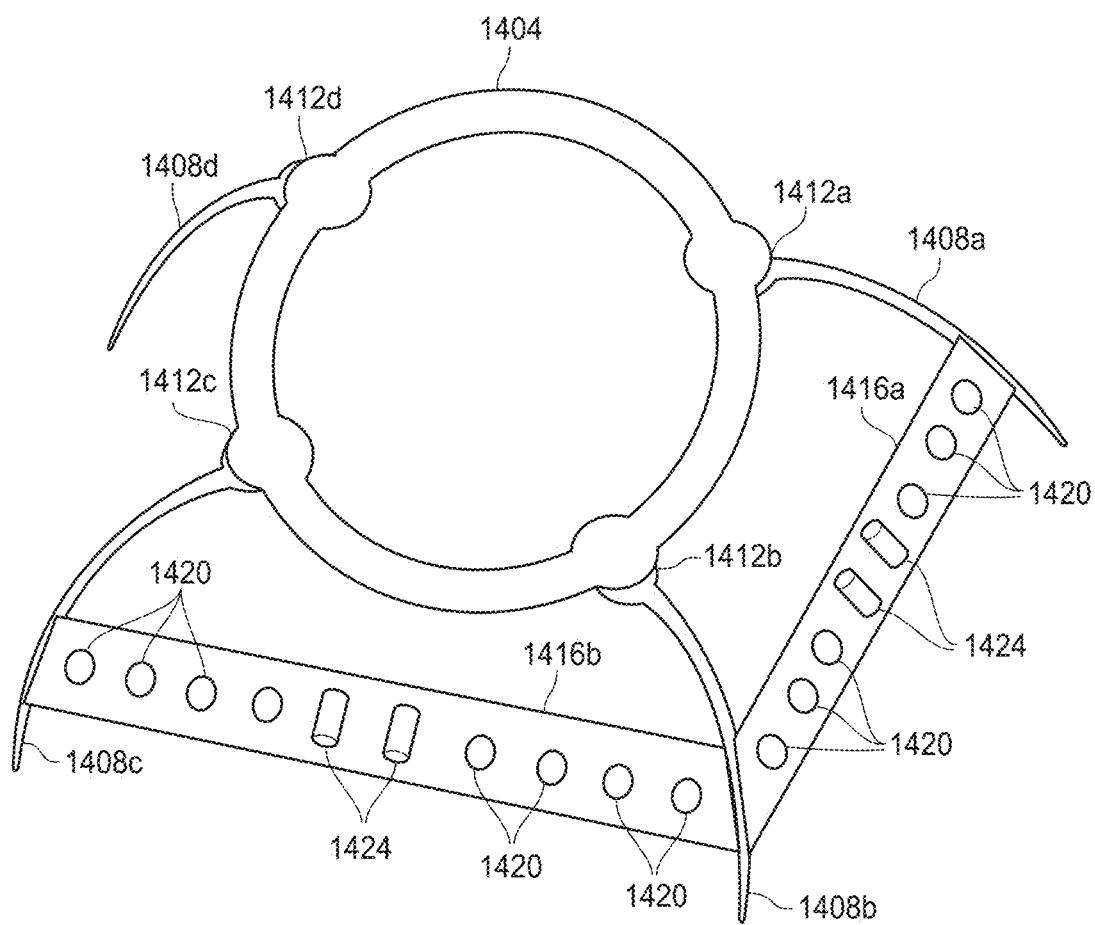
FIG. 17 illustrates an example portable device via which the system can deliver OMF therapy.

Portable OMF devices may allow for the application of OMF therapy in a hospital or clinic in pre- and/or post-surgical treatments, as well as in outpatient care or for ambulatory patient treatment at home. FIG. 17 illustrates an embodiment of a portable OMF device 1400 having an adjustable frame with a central ring 1404 and multiple semi-polygonal antero-posterior adjustable ribs 1408a-1408d that are rotatable and may be fixed in place at desired positions and angles. The portable OMF device 1400 of FIG. 17 may be useful in providing OMF treatment to a patient's head, and the adjustable ribs 1408a-1408d may be positioned to fit on and around a patient's head depending on the size of the patient's head. In embodiments, the adjustable ribs 1408a-1408d may be physically coupled to the central ring 1404 by ball joints 1412a-1412d, as illustrated in FIG. 17. In other embodiments the adjustable ribs 1408a-1408d may be physically coupled to the central ring 1404 by another type of joint, socket, or method allowing for the adjustability of the position and angle of the adjustable ribs 1408a-1408d. It may be desirable to fix the position of the adjustable ribs 1408a-1408d, after adjusting the adjustable ribs 1408a-1408d, for applying OMF treatment to a patient. Therefore, the portable OMF device 1400 may include set screws, bolts, or another physical locking mechanism that may be engaged to lock the adjustable ribs 1408a-1408d in a fixed position, and disengaged to allow for adjusting of the adjustable ribs 1408a-1408d.

The portable OMF device 1400 of FIG. 17 further includes removable plastic inserts 1416a and 1416b that may by clipped onto the adjustable ribs 1408a-1408d and may be configured to span a space between the adjustable ribs 1408a-1408d. The removable plastic inserts 1416a and 1416b contain perforations 1420 by which oncoscillators 1424 may be attached to the removable plastic inserts 1416a and 1416b. The perforations 1420 in the removable plastic inserts 1416a and 1416b enable the attachment the oncoscillators 1424 at any location and in any orientation close to a patient's scalp (i.e., ~0.5 cm over the scalp) using snap-on connectors protruding from the top of each oncoscillator 1424. While described as being attached using snap-on connectors, in embodiments, the oncoscillators 1424 may be attached to the plastic inserts 1416a and 1416b by a hook, Velcro, a temporary adhesive, adhesive tape, a clip, or another type of physical fastener. In embodiments, the plastic inserts 1416a and 1416b may have pockets that the oncoscillators 1424 may be placed in for administering OMF treatment to a region. In addition to spanning spaces between the adjustable ribs 1408a-1408d, removable plastic inserts may also be attached to the central ring 1404 and may span the area inside of the central ring 1404 to provide OMF to a desired region of a patient (e.g., the top of a scalp).

As compared to a head mount or hardness made of plastic or cloth, for example, the device 1400 provides higher durability and increased convenience of rigidly fixing ribs supporting oncoscillators relative to the patient's head.

The following description of is one example application of providing OMF treatment to a patient using the portable OMF device 1400 of FIG. 17, and is meant to be exemplary in nature and is not intended to be limiting of the embodiments disclosed herein, nor exhaustive of all of the embodiments conceivable from the disclosure. In an example application of OMF using the portable OMF device 1400 of FIG. 17, one oncoscillator 1424 may be attached to one of the plastic inserts 1416a and 1416b configured to provide OMFs to the center of a scalp projection of a tumor. Four other oncoscillators 1424 may be attached to plastic inserts (e.g., the plastic inserts 1416a and 1416b) 3 cm from the center of the scalp projection of the tumor, each of the four oncoscillators being away from the center of the scalp projection of the tumor in all four perpendicular directions. Up to 10 other oncoscillators are then positioned, evenly spaced, around the rest of the scalp at 3 cm distances from each other, fanning out from the center to provide OMF treatment coverage to the entire head of a patient.

In embodiments, the portable OMF device 1400 may be a freestanding device supported by a patient's body, or the portable OMF device may be interchangeably attachable to the headboard of a bed, a designated stand, a chair, or another physical support structure. In embodiments, the portable OMF device 1400 may be made of plastic, aluminum, or another non-magnetic material as not to interfere with the application of OMF treatment to a patient. In embodiments, the removable plastic inserts 1416a and 1416b may be physically connected to the adjustable ribs by fasteners, adhesive, clips, being wrapped around the ribs, elastic bands, or another physical connection. While described herein as removable plastic inserts, the removable inserts may be made of other materials such as aluminum, a cloth or fabric, a Velcro strip, an elastic material or fabric, or another non-magnetic material.

In embodiments, a device controller with multiple electrical channels allows simultaneous activation of a plurality of oncoscillators. In the example application of OMF described above, the device controller should have at least 15 electrical channels to control all 15 oncoscillators. The electrical channels may be hardware or software-based communication channels. The controller may include a memory with computer readable instructions stored thereon, designed to apply OMF treatment to a patient using the portable OMF device 1400 of FIG. 17. The controller may include a processor that executes the computer readable instructions to deploy a prescribed stimulus protocol for a specific patient. The controller may be implemented in hardware and/or in an application or software on a Bluetooth-connected device (e.g., a tablet, smart phone, laptop, etc.). In embodiments, the controller may have built-in safeguards, such as face recognition utilizing a camera (e.g., a cell phone camera, laptop camera, etc.) or automatic secure feedback of self-image, timed locking of the device and device function feedback, by secure text, to prevent use by non-intended users, and to prevent misuse (e.g., application of OMF treatment beyond what has been prescribed). Additionally, device function feedback may be further obtained and analyzed by the controller to ensure treatment compliance and proper functioning of the device.

The following list of aspects reflects a variety of the embodiments explicitly contemplated by the present disclosure. Those of ordinary skill in the art will readily appreciate that the aspects below are neither limiting of the embodiments disclosed herein, nor exhaustive of all of the embodiments conceivable from the disclosure above, but are instead meant to be exemplary in nature.

1. A method for disrupting mitochondrial function in cells, the method comprising: causing, by controlling hardware, a magnet to oscillate so as to generate an oscillating magnetic field; and applying the oscillating magnetic field to a volume of tissue including cells with a mitochondrial impairment to trigger apoptosis in the cells with the mitochondrial impairment.

2. The method of aspect 1, wherein applying the oscillating magnetic field to the tissue includes altering the electron flow in the tissue.

3. The method of aspect 2, wherein altering the electron flow in the tissue includes opening of mitochondrial membrane permeability transition pore and inducing rapid fluctuation or sustained depolarization of a mitochondrial membrane potential (MMP) in the tissue to cause fragmentation of mitochondrial networks in the tissue, wherein the altering of the electron flow causes apoptosis in the cells with the mitochondrial impairment and not in non-cancerous cells without mitochondrial impairment.

4. The method of aspect 2, wherein altering the electron flow in the tissue decreases glucose-derived 13C-acetyl-CoA synthesis in mitochondria of the tissue.

5. The method of aspect 2, wherein alteration of the electron flow in the tissue increases glycolytic flux in the tissue.

6. The method of aspect 2, wherein altering the electron flow in the tissue increases superoxide, peroxide and other reactive oxygen species generation.

7. The method of any one of aspects 1 to 6, wherein the cells with the mitochondrial impairment are cancer cells.

8. The method of aspect 7, wherein the cancer cells are glioblastoma (GBM) cells.

9. The method of aspect 7, wherein the cancer cells are non-small cell lung carcinoma, malignant meningioma, diffuse intrinsic pontine glioma, carcinoma of the breast and other cancer cells.

10. The method of any one of aspects 1 to 9, wherein the magnet is axially magnetized at 1.2 Tesla or more.

11. The method of any one of aspects 1 to 10, wherein the magnet is diametrically magnetized at 1.2 Tesla or more.

12. The method of any one of aspects 1 to 11, wherein the magnet is a rare earth permanent magnet.

13. The method of aspect 11, wherein the magnet is N52 neodymium.

14. The method of any one of aspects 1 to 13, wherein causing the magnet to oscillate includes oscillating the magnet using an electric motor with a motor shaft, wherein the magnet is mounted to the motor shaft.

15. The method of aspect 14, wherein causing the magnet to oscillate includes rotating the magnet at a rate of between 300 RPM and 24,000 RPM.

16. The method of aspect 14, wherein the magnet is mounted to the motor shaft either perpendicularly to the motor shaft, coaxially with the motor shaft, or longitudinally to the motor shaft.

17. The method of aspect 14, wherein causing the magnet to oscillate includes causing the magnet to oscillate either perpendicularly to the motor shaft, coaxially with the motor shaft, or longitudinally to the motor shaft.

18. The method of any one of aspects 1 to 17, wherein applying the oscillating magnetic field to the volume of tissue includes applying the oscillating magnetic field continuously during of a period of between 1 minute and 18 hours.

19. The method of any one of aspects 1 to 18, wherein applying the oscillating magnetic field to the volume of tissue includes applying a series of stimulus pulses of a first duration separated by inter-stimulus pulse intervals of a second duration, wherein the first duration is in a range of 10 milliseconds to 5 seconds, and the second duration is in a range of 10 milliseconds to 10 minutes.

20. The method of aspect 19, wherein applying the series of stimulus pulses includes dynamically varying, during a treatment session, at least one of (i) the first duration, (ii) the second duration, or (iii) a rate at which the magnet oscillates.

21. The method of any one of aspects 1 to 20, wherein applying the oscillating magnetic field to the tissue includes operating a stimulator including the magnet in one of (i) a wearable helmet, (ii) a brace, or (iii) a belt.

22. The method of any one of aspects 1 to 21, wherein applying the oscillating magnetic field to the tissue includes operating a stimulator including the magnet in a bridge frame straddling a body part.

23. The method of any one of aspects 1 to 22, wherein the magnet is integrated into an end of an intraoperative probe.

24. The method of any one of aspects 1 to 23, wherein the magnet is a first magnet included in a plurality of magnets, the method further comprising: causing, by the controlling hardware, the plurality of magnets to oscillate to generate respective components of the oscillating magnetic field.

25. The method of aspect 24, wherein each pair in the plurality of magnets is separated by at least 2 cm at respective magnetic ends.

26. The method of aspect 24 or aspect 25, wherein the plurality of magnets includes a pair of magnets oriented at an angle of at least 60 degrees relative to each other.

27. The method of any one of aspects 24 to 26, wherein applying the oscillating magnetic field to the volume of tissue includes placing the plurality of magnets around the volume of tissue.

28. The method of any one of aspects 24 to 27, wherein generate respective components of the oscillating magnetic field includes varying at least one of (i) a rate of oscillation, (ii) a time of activation, (iii) a duration of stimulus pulses, or (iv) a duration of inter-stimulus pulse intervals for a certain magnet in the plurality of magnets independently of at least one other magnet in the plurality of magnets.

29. The method of any one of aspects 24 to 28, wherein applying the oscillating magnetic field to the volume of tissue includes: causing individual magnets in the plurality of magnets to oscillate in accordance with a programmed protocol specific to a patient.

30. The method of any one of aspects 1 to 29, further comprising: introducing a chemical into the volume of tissue including cells with the mitochondrial impairment.

31. The method of aspect 30, wherein the chemical is a ketone body.

32. A system for disrupting mitochondrial function in cells, the system comprising: at least one stimulator including a magnet; and a controlling hardware configured to cause the magnet to oscillate so as to generate an oscillating magnetic field that, when applied to a volume of tissue including cells with a mitochondrial impairment, triggers apoptosis in the cells with the mitochondrial impairment.

33. The system of aspect 32, wherein the magnet is axially magnetized at 1.2 Tesla or more.

34. The system of aspect 32 or aspect 33, wherein the magnet is diametrically magnetized at 1.2 Tesla or more.

35. The system of any one of aspects 32 to 34, wherein the magnet is a rare earth permanent magnet.

36. The system of any one of aspects 32 to 35, wherein the magnet is N52 neodymium.

37. The system of any one of aspects 32 to 36, wherein the stimulator includes an electric motor with a motor shaft, wherein the magnet is mounted to the motor shaft.

38. The system of any aspect to 37, wherein the controlling hardware causes the magnet to oscillate includes rotating the magnet at a rate of between 300 RPM and 24,000 RPM.

39. The system of aspect 37 or aspect 38, the magnet is mounted to the motor shaft either perpendicularly to the motor shaft, coaxially with the motor shaft, or longitudinally to the motor shaft.

40. The system of any one of aspects 37 to 39, wherein the controlling hardware causes the magnet to oscillate either perpendicularly to the motor shaft, coaxially with the motor shaft, or longitudinally to the motor shaft.

41. The system of any one of aspects 32 to 40, wherein the controlling hardware is configured to apply the oscillating magnetic field to the volume of tissue continuously during of a period of between 1 minute and 18 hours.

42. The system of any one of aspects 32 to 41, wherein the controlling hardware is configure to generate a series of stimulus pulses of a first duration separated by inter-stimulus pulse intervals of a second duration, wherein the first duration is in a range of 10 milliseconds to 5 seconds, and the second duration is in a range of 10 milliseconds to 10 minutes.

43. The system of any one of aspects 32 to 42, wherein the controlling hardware is configured to dynamically vary during a treatment session, at least one of (i) the first duration, (ii) the second duration, or (iii) a rate at which the magnet oscillates.

44. The system of any one of aspects 32 to 43, further comprising: a plurality of stimulators including the at least one stimulator, each stimulator including a respective magnet; wherein the controlling hardware is configured to activate the plurality of stimulators according to a stimulation pattern.

45. The system of aspect 44, wherein the plurality of stimulators are mounted in one of (i) a wearable helmet, (ii) a brace, or (iii) a belt.

46. The system of aspect 44 or aspect 45, wherein each pair in the plurality of magnets is separated by at least 2 cm at respective magnetic ends.

47. The system of any one of aspects 44 to 46, wherein plurality of stimulators includes a pair of magnets oriented at an angle of at least 60 degrees relative to each other.

48. The system of any one of aspects 32 to 47, wherein the controlling hardware includes: one or more processors, and a non-transitory computer-readable medium storing software instructions that, when executed by the one or more processors, cause the controlling hardware to generate signals that cause the magnet to oscillate.

49. The system of aspect 48, further comprising: a peripheral interface via which the controlling hardware provides the signals to the magnet.

50. A method for disrupting mitochondrial function in cells, the method comprising: introducing a ketone body into a volume of tissue including cells with a mitochondrial impairment; generating, by controlling hardware, an alteration of electron flow parameterized to treat the tumor by at least one of (i) preventing cell division or growth, or (ii) causing cell death; and applying an oscillating magnetic field to the volume of tissue, wherein the chemical potentiates the treatment of the tumor.

51. The method of aspect 50, wherein the ketone body is a β-hydroxybutyrate.

52. The method of aspect 50 or 51, wherein alteration of electron flow in the tissue includes altering the electron flow using an oscillating magnetic field.

53. The method of aspect 52, wherein alteration of electron flow using the oscillating magnetic field includes causing, by the controlling hardware, a magnet to oscillate so as to generate the oscillating magnetic field.

54. The method of aspect 53, wherein alteration of electron flow in the tissue includes opening of the mitochondrial permeability transition pore and inducing rapid fluctuation or sustained depolarization of a mitochondrial membrane potential (MMP) in the tissue to cause fragmentation of mitochondrial networks in the tissue, wherein the inducing rapid fluctuation or sustained depolarization of the MMP causes apoptosis in the cells with the mitochondrial impairment and not in non-cancerous cells without mitochondrial impairment.

55. The method of aspect 51 to 53, wherein alteration of electron flow in the tissue decreases glucose-derived 13C-acetyl-CoA synthesis in mitochondria of the tissue.

56. The method of aspect 53, wherein alteration of electron flow in the tissue increases glycolytic flux in the tissue.

57. The method of aspect 53, wherein alteration of electron flow in the tissue increases superoxide, peroxide and other reactive oxygen species generation.

58. The method of any one of aspects 50 to 57, wherein the cells with the mitochondrial impairment are cancer cells.

59. The method of aspect 58, wherein the cancer cells are glioblastoma (GBM) cells.

60. The method of aspect 58, wherein the cancer cells are non-small cell lung carcinoma, malignant meningioma, diffuse intrinsic pontine glioma, carcinoma of the breast and other cancer cells.

61. The method of any one of aspects 50 to 60, wherein the magnet is axially magnetized at 1.2 Tesla or more.

62. The method of any one of aspects 50 to 60, wherein the magnet is diametrically magnetized at 1.2 Tesla or more.

63. The method of any one of aspects 50 to 62, wherein the magnet is a rare earth permanent magnet.

64. The method of aspect 63, wherein the magnet is N52 neodymium.

65. The method of any one of aspects 50 to 64, wherein causing the magnet to oscillate includes oscillating the magnet using an electric motor with a motor shaft, wherein the magnet is mounted to the motor shaft.

66. The method of any one of aspects 50 to 65, wherein causing the magnet to oscillate includes rotating the magnet at a rate of between 300 RPM and 24,000 RPM.

67. The method of aspect 65, wherein the magnet is mounted to the motor shaft either perpendicularly to the motor shaft, coaxially with the motor shaft, or longitudinally to the motor shaft.

68. The method of aspect 65 or aspect 67, wherein causing the magnet to oscillate includes causing the magnet to oscillate either perpendicularly to the motor shaft, coaxially with the motor shaft, or longitudinally to the motor shaft.

69. The method of any one of aspects 50 to 68, wherein applying the oscillating magnetic field to the volume of tissue includes applying the oscillating magnetic field continuously during of a period of between 1 minute and 18 hours.

70. The method of any one of aspects 50 to 68, wherein applying the oscillating magnetic field to the volume of tissue includes applying a series of stimulus pulses of a first duration separated by inter-stimulus pulse intervals of a second duration, wherein the first duration is in a range of 10 milliseconds to 5 seconds, and the second duration is in a range of 10 milliseconds to 10 minutes.

71. The method of aspect 70, wherein applying the series of stimulus pulses includes dynamically varying, during a treatment session, at least one of (i) the first duration, (ii) the second duration, or (iii) a rate at which the magnet oscillates.

72. The method of any one of aspects 50 to 71, wherein applying the oscillating magnetic field to the tissue includes operating a stimulator including the magnet in one of (i) a wearable helmet, (ii) a brace, or (iii) a belt.

73. The method of any one of aspects 50 to 72, wherein applying the oscillating magnetic field to the tissue includes operating a stimulator including the magnet in a bridge frame straddling a body part.

74. The method of any one of aspects 50 to 72, wherein the magnet is integrated into an end of an intraoperative probe.

75. The method of any one of aspects 50 to 74, wherein the magnet is a first magnet included in a plurality of magnets, the method further comprising: causing, by the controlling hardware, the plurality of magnets to oscillate to generate respective components of the oscillating magnetic field.

76. The method of aspect 75, wherein each pair in the plurality of magnets is separated by at least 2 cm at respective magnetic ends.

77. The method of aspect 75 or aspect 76, wherein the plurality of magnets includes a pair of magnets oriented at an angle of at least 60 degrees relative to each other 78. The method of any one of aspects 75 to 77, wherein applying the oscillating magnetic field to the volume of tissue includes placing the plurality of magnets around the volume of tissue.

79. The method of any one of aspects 75 to 78, wherein generate respective components of the oscillating magnetic field includes varying at least one of (i) a rate of oscillation, (ii) a time of activation, (iii) a duration of stimulus pulses, or (iv) a duration of inter-stimulus pulse intervals for a certain magnet in the plurality of magnets independently of at least one other magnet in the plurality of magnets.

80. The method of any one of aspects 75 to 79, wherein applying the oscillating magnetic field to the volume of tissue includes: causing individual magnets in the plurality of magnets to oscillate in accordance with a programmed protocol specific to a patient.

81. The method of any one of aspects 50 to 80, wherein applying the oscillating magnetic field to the volume of tissue comprises applying an oscillating magnetic field configured to trigger apoptosis in the cells with the mitochondrial impairment.

82. A device for providing an oscillating magnetic field (OMF) treatment to a patient, the device comprising a plurality of ribs configured to articulate relative to a frame so as to fit around a head of a patient; and a plurality of inserts, each configured to attach to at least one of the plurality of ribs and support one or more magnetic stimulators to generate an oscillating magnetic field for application to the head of the patient.

83. The device of aspect 82, wherein the plurality of ribs are in an antero-posterior orientation relative to the head.

84. The device of aspect 82, wherein the plurality of ribs are connected to the frame by respective ball joints.

85. The device of aspect 82, wherein the plurality of ribs are configured to be angularly fixed relative to the frame using a locking mechanism.

86. The device of aspect 82, wherein the frame is a ring.

87. The device of aspect 82, wherein the plurality of ribs are made of aluminum.

88. The device of aspect 82, wherein the plurality of ribs are made of non-magnetic material.

89. The device of aspect 82, wherein the plurality of inserts are made of plastic.

What is claimed is:

1. A method for disrupting mitochondrial function in cells, the method comprising:
   causing, by controlling hardware, a magnet to generate an oscillating magnetic field (OMF), including ramping a frequency of the OMF to a peak frequency of between 250 HZ and 350 Hz, over a period of 75 ms to 100 ms; and
   applying the oscillating magnetic field to a volume of tissue including cells with a mitochondrial impairment to trigger apoptosis in the cells with the mitochondrial impairment.

2. The method of claim 1, wherein applying the OMF to the tissue includes applying the OMF in a manner that results in inducing an alteration of electron flow in the tissue.

3. The method of claim 2, wherein applying the OMF to the tissue includes applying the OMF in a manner that causes apoptosis in the cells with the mitochondrial impairment and not in non-cancerous cells without mitochondrial impairment.

4. The method of claim 1, wherein the magnet is a rare earth permanent magnet.

5. The method of claim 1, wherein causing the magnet to generate the OMF includes oscillating the magnet using an electric motor with a motor shaft, wherein the magnet is mounted to the motor shaft.

6. The method of claim 5, wherein causing the magnet to generate the OMF includes causing the magnet to oscillate either perpendicularly to the motor shaft, coaxially with the motor shaft, or longitudinally to the motor shaft.

7. The method of claim 1, wherein applying the oscillating magnetic field to the volume of tissue includes applying the oscillating magnetic field continuously during of a period of between 1 minute and 18 hours.

8. The method of claim 1, wherein applying the oscillating magnetic field to the volume of tissue includes generating a sequence of pulses with a pulse length of approximately 250 ms.

9. The method of claim 8, wherein generating the sequence of pulses includes generating the pulses with a pulse interval of approximately 250 ms.

10. The method of claim 1, wherein applying the oscillating magnetic field to the volume of tissue includes applying a series of stimulus pulses of a first duration separated by inter-stimulus pulse intervals of a second duration, wherein the first duration is in a range of 10 milliseconds to 5 seconds, and the second duration is in a range of 10 milliseconds to 10 minutes.

11. The method of claim 1, further comprising:
   introducing a chemical into the volume of tissue including cells with the mitochondrial impairment, wherein the chemical is a ketone body or free fatty acid.

12. The method of claim 11, wherein the ketone body is a b-hydroxybutyrate.

13. The method of claim 11, wherein the free fatty acid is octanoate or palmitate.

14. A system for disrupting mitochondrial function in cells, the system comprising:
   at least one stimulator including a magnet; and
   a controlling hardware configured to cause the magnet to generate an oscillating magnetic field (OMF), including ramp a frequency of the OMF to a peak frequency of between 250 HZ and 350 Hz, over a period of 75 ms to 100 ms, wherein the OMF, when applied to a volume of tissue including cells with a mitochondrial impairment, triggers apoptosis in the cells with the mitochondrial impairment.

15. The system of claim 14, wherein the controlling hardware causes the magnet to generate a sequence of pulses with a pulse length of approximately 250 ms and a pulse interval of approximately 250 ms.

16. The system of claim 14, wherein the controlling hardware causes the magnet to generate a series of stimulus pulses of a first duration separated by inter-stimulus pulse intervals of a second duration, wherein the first duration is in a range of 10 milliseconds to 5 seconds, and the second duration is in a range of 10 milliseconds to 10 minutes.

17. The system of claim 14, including a pair of magnets oriented at an angle of at least 60 degrees relative to each other.

* * * * *